United States Patent
Ma et al.

(10) Patent No.: US 10,111,923 B2
(45) Date of Patent: Oct. 30, 2018

(54) **COMPOSITIONS COMPRISING *CYCLOCARYA PALIURUS* EXTRACT AND PREPARATION METHOD AND USES THEREOF**

(71) Applicant: Infinitus (China) Company LTD, Jiang Men, Guangdong (CN)

(72) Inventors: Chung Wah Ma, Guangzhou (CN); Zhen Luo, Guangzhou (CN); Xia Zheng, Guangzhou (CN); Xiaolei Guo, Guangzhou (CN)

(73) Assignee: INFINITUS (CHINA) COMPANY LTD, Jiangmen (CN)

( * ) Notice: Subject to any disclaimer, the term of this patent is extended or adjusted under 35 U.S.C. 154(b) by 43 days.

(21) Appl. No.: 15/128,866

(22) PCT Filed: Apr. 28, 2016

(86) PCT No.: PCT/CN2016/080551
§ 371 (c)(1),
(2) Date: Sep. 23, 2016

(87) PCT Pub. No.: WO2016/173511
PCT Pub. Date: Nov. 3, 2016

(65) Prior Publication Data
US 2017/0173103 A1 Jun. 22, 2017

(30) Foreign Application Priority Data

Apr. 29, 2015 (CN) .......................... 2015 1 0212607
Apr. 29, 2015 (CN) .......................... 2015 1 0213059
Apr. 29, 2015 (CN) .......................... 2015 1 0214436

(51) Int. Cl.
| | | |
|---|---|---|
| A61K 36/00 | (2006.01) |
| A61K 36/82 | (2006.01) |
| A61K 36/752 | (2006.01) |
| A61K 36/8984 | (2006.01) |
| A61K 36/52 | (2006.01) |
| A61K 36/605 | (2006.01) |
| A61K 9/16 | (2006.01) |
| A61K 9/48 | (2006.01) |
| A23L 33/00 | (2016.01) |
| A47G 19/16 | (2006.01) |
| B65D 85/808 | (2006.01) |
| A61K 36/488 | (2006.01) |
| A61K 36/88 | (2006.01) |
| A61K 36/8969 | (2006.01) |
| A61K 36/185 | (2006.01) |
| A61K 36/42 | (2006.01) |
| A61P 3/06 | (2006.01) |
| A61P 9/12 | (2006.01) |
| A61P 3/10 | (2006.01) |

(52) U.S. Cl.
CPC .............. *A61K 36/82* (2013.01); *A23L 33/40* (2016.08); *A47G 19/16* (2013.01); *A61K 9/16* (2013.01); *A61K 9/1623* (2013.01); *A61K 9/1652* (2013.01); *A61K 9/485* (2013.01); *A61K 9/4808* (2013.01); *A61K 9/4825* (2013.01); *A61K 9/4833* (2013.01); *A61K 9/4866* (2013.01); *A61K 36/185* (2013.01); *A61K 36/42* (2013.01); *A61K 36/488* (2013.01); *A61K 36/52* (2013.01); *A61K 36/605* (2013.01); *A61K 36/752* (2013.01); *A61K 36/88* (2013.01); *A61K 36/8969* (2013.01); *A61K 36/8984* (2013.01); *A61P 3/06* (2018.01); *A61P 3/10* (2018.01); *A61P 9/12* (2018.01); *B65D 85/808* (2013.01); *A23V 2002/00* (2013.01); *A61K 2236/00* (2013.01); *A61K 2236/13* (2013.01); *A61K 2236/15* (2013.01); *A61K 2236/17* (2013.01); *A61K 2236/51* (2013.01); *H05K 999/99* (2013.01)

(58) Field of Classification Search
CPC ....................................................... A61K 36/00
See application file for complete search history.

(56) References Cited

U.S. PATENT DOCUMENTS

| | | |
|---|---|---|
| 2005/0048137 A1 | 3/2005 | Wu |
| 2009/0004281 A1 | 1/2009 | Nghiem et al. |
| 2011/0027305 A1 | 2/2011 | Lee |
| 2017/0173101 A1 | 6/2017 | Zhen et al. |
| 2017/0202897 A1 | 7/2017 | Zheng et al. |

FOREIGN PATENT DOCUMENTS

| | | | |
|---|---|---|---|
| CN | 1389146 A | | 1/2003 |
| CN | 101028363 A | | 9/2007 |
| CN | 101433332 A | | 5/2009 |
| CN | 101744888 A | | 6/2010 |
| CN | 101879278 A | * | 11/2010 |
| CN | 101979639 A | | 2/2011 |
| CN | 102000168 A | * | 4/2011 |
| CN | 102048958 A | | 5/2011 |

(Continued)

OTHER PUBLICATIONS

Shu, Antihyperglycemic effects of total flavonoids from Polygonatum odoratum in STZ and alloxan-induced diabetic rats. Journal of ethnopharmacology, (Jul. 30, 2009) vol. 124, No. 3, pp. 539-543 (Year: 2009).*

(Continued)

*Primary Examiner* — Qiuwen Mi
(74) *Attorney, Agent, or Firm* — Morrison & Foerster LLP

(57) ABSTRACT

Compositions and preparation method thereof, said compositions comprise herb extract from a mixture comprising *Cyclocarya paliurus* leaf and one or two herbs selected from the group consisting of Puerariae lobatae Radix and Polygonati odorati Rhizoma, said compositions can treat diabetes, hyperglycemia, hypertension and/or hyperlipidemia.

7 Claims, 4 Drawing Sheets

(56) References Cited

FOREIGN PATENT DOCUMENTS

| CN | 102552388 | A | | 7/2012 |
|---|---|---|---|---|
| CN | 102754710 | A | | 10/2012 |
| CN | 102525945 | B | * | 5/2013 |
| CN | 103893620 | A | * | 7/2014 |
| CN | 103920151 | A | | 7/2014 |
| CN | 103989980 | A | | 8/2014 |
| CN | 104069370 | A | | 10/2014 |
| CN | 104187361 | A | | 12/2014 |
| CN | 104189744 | A | | 12/2014 |
| CN | 104784258 | A | | 7/2015 |
| CN | 104839662 | A | | 8/2015 |
| CN | 104855974 | A | | 8/2015 |
| CN | 104996993 | A | | 10/2015 |
| WO | WO-2015/003324 | A1 | | 1/2015 |
| WO | WO-2016/173509 | A1 | | 11/2016 |
| WO | WO-2016/173511 | A1 | | 11/2016 |
| WO | WO-2016/173512 | A1 | | 11/2016 |

OTHER PUBLICATIONS

Li-Hua, C. et al. (Dec. 31, 2005). "The Distributing of Natural Hypoglycemic Functional Factors," *Modern Food Science and Technology* 21(3):172-175, (English Abstract only).

Sen, M.A. (Apr. 30, 2010). "Studies on Reducing Blood Sugar Effect of Citrus Peel and Dried Tangerine Peel," *Journal of Wuyi College* 29(2):18-20, (English Abstract only).

Zhou, W. et.al (Apr. 30, 2013). "Progress of Effective Ingredients of Traditional Chinese Medicine on Diabetes Therapy," *Journal of Guangdong Pharmaceutical University* 29(2):219-222, (English Abstract only).

International Search Report dated Jul. 15, 2016, for PCT Application No. PCT/CN2016/080547 filed Apr. 28, 2016, six pages.

International Search Report dated Jul. 15, 2016, for PCT Application No. PCT/CN2016/080553 filed Apr. 28, 2016, six pages.

International Search Report dated Jul. 22, 2016, for PCT Application No. PCT/CN2016/080551, filed Apr. 28, 2016, six pages.

Written Opinion of the International Searching Authority dated Jul. 15, 2016, for PCT Application No. PCT/CN2016/080547 filed Apr. 28, 2016, five pages.

Written Opinion of the International Searching Authority dated Jul. 22, 2016, for PCT Application No. PCT/CN2016/080551 filed Apr. 28, 2016, seven pages.

Written Opinion of the International Searching Authority dated Jul. 15, 2016, for PCT Application No. PCT/CN2016/080553 filed Apr. 28, 2016, seven pages.

Abou-Seif, M.A.M. et al. (2008). "Hypoglycemic and Metabolic Activity of Aqueous Extract of *Morus alba* in Streptozotocin-Diabetic Rats," *Bioscience, Biotechnology Research Asia* 5(1):139-144. English Replacement Paper for reference: Abou-Seif, M.A.M. et al. (Jun. 1, 2009). "Hypoglycemic and Metabolic Activity of Aqueous Extract of *Morus alba* in Streptozotocin-Diabetic Rats," *Medicinal & Aromatic Plants Abstracts* 31(3).

Kim, E. et al. (1999). "Purification and Characterization of Moran 20K from *Morus alba*," *Arch Pharm Res* 22(1):9-12.

Son, Hee-Kyoung et al. (Aug. 30, 2014). "Anti-Diabetic Effect of the Mixture of Mulberry Leaf and Green Tea Powder in Rats with Streptozotocin-Induced Diabetes," *Korean Journal of Food Preservation* 21(4):549-559, (English Abstract only).

Wang, Qingqing et al. (2013; e-published on Oct. 30, 2013). "Antihyperglycemic, Antihyperlipidemic and Antioxidant Effects of Ethanol and Aqueous Extracts of *Cyclocarya paliurus* leaves in Type 2 Diabetic Rats," *Journal of Ethnopharmacology* 150(3):1119-1127.

European Search Report dated Dec. 7, 2017 for EP Application No. 16785075.9, thirteen pages.

European Search Report dated Dec. 7, 2017 for EP Application No. 16785076.7, eleven pages.

European Search Report dated Mar. 12, 2018 for EP Application No. 16785077.5, nine pages.

* cited by examiner

| Chinese Herbal Medicine | Chinese Name | Chinese Herbal Medicine | Chinese Name |
|---|---|---|---|
| Aloe | 芦荟 | *Ligustri lucidi Fructus* | 女贞子 |
| *Anemarrhenae Rhizoma* | 知母 | Longan leaves | 龙眼叶 |
| *Angelicae sinensis Radix* | 当归 | *Lycii Fructus* | 枸杞子 |
| *Astragali Radix* | 黄芪 | *Lycii Folium* | 枸杞叶 |
| *Atractylodis Rhizoma* | 苍术 | *Mori Cortex* | 桑白皮 |
| Balsam pear | 苦瓜 | *Mori Folium* | 桑叶 |
| Black Tea | 红茶 | *Mume Fructus* | 乌梅 |
| *Broadleaf Holly* leaf | 苦丁茶 | *Myrica rubra* leaves | 杨梅叶 |
| Buckwheat leaves | 荞麦叶 | *Notoginseng Radix et Rhizoma* | 三七 |
| Celery | 芹菜 | *Ophiopogonis Radix* | 麦门冬 |
| *Chuanxiong Rhizoma* | 川芎 | *Paeoniae Radix alba* | 白芍 |
| *Citri Reticulatae Pericarpium* | 陈皮 | *Panacis Quinquefolii Radix* | 西洋参 |
| Corn Stigma | 玉米须 | *Polygonati odorati Rhizoma* | 玉竹 |
| *Corni Fructus* | 山茱萸 | *Polygonati Rhizoma* | 黄精 |
| *Cyclocarya paliurus* leaves | 青钱柳叶 | *Poria* | 茯苓 |
| *Dendrobii Caulis* | 石斛 | Prepared Rhubarb | 制大黄 |
| *Dioscoreae Rhizoma* | 山药 | *Puerariae lobatae Radix* | 葛根 |
| *Eriobotryae Folium* | 枇杷叶 | Pumpkin | 南瓜 |
| *Fagopyrum tataricum* | 苦荞麦 | *Rehmanniae Radix* | 生地黄 |
| Garlic | 大蒜 | *Rhodiolae Crenulatae Radix et Rhizoma* | 红景天 |
| *Ginkgo Folium* | 银杏叶 | *Schisandrae chinensis Fructus* | 五味子 |
| *Ginseng Radix et Rhizoma* | 人参 | *Scrophulariae Radix* | 玄参 |
| Green Tea | 绿茶 | *Siraitiae Fructus* | 罗汉果 |
| *Gynostemma pentaphyllum* | 绞股蓝 | Sweet Potato leaves | 番薯叶 |
| *Hericium erinaceus* | 猴头菇 | *Tremella* | 银耳 |
| Konjac | 魔芋 | *Tribuli Fructus* | 蒺藜 |
| *Laminariae Thallus Eckloniae Thallus* | 昆布 | | |

FIG 1

COMPOSITIONS COMPRISING *CYCLOCARYA PALIURUS* EXTRACT AND PREPARATION METHOD AND USES THEREOF

CROSS-REFERENCE TO RELATED APPLICATIONS

This application is a National Phase application under 35 U.S.C. § 371 of International Application No. PCT/CN2016/080551 filed Apr. 28, 2016, which claims priority to People's Republic of China Patent Application No. 201510212607.0 filed Apr. 29, 2015, People's Republic of China Patent Application No. 201510214436.5 filed Apr. 29, 2015, and People's Republic of China Patent Application No. 201510213059.3 filed Apr. 29, 2015, the disclosures of each of which are hereby incorporated herein by reference in their entireties.

FIELD OF THE INVENTION

The present invention relates to the field of herbal medicine and herbal nutritional composition. In particular, the present invention relates to processed herbal compositions (such as an extract) comprising *Cyclocarya paliurus* leaves and other herbs (such as Puerariae lobatae Radix and Polygonati odorati Rhizoma), and their use in lowering blood sugar and treating diabetes, hyperglycemia, hypertension and/or hyperlipidemia.

BACKGROUND

Diabetes mellitus is a chronic metabolic disease characterized by high levels of blood sugar in afflicted individuals. Long-term elevated sugar levels in the blood can lead to serious damage to many parts of the body, including blood vessels, kidney, and the nervous system. Because of rapid economic growth and urbanization, an increasing population of the world adopts a high-carbohydrate diet and a sedentary life style, which are major factors contributing to a global epidemic of diabetes. According to the World Health Organization, more than 347 million people worldwide live with diabetes, and an estimated 1.5 million deaths were directly caused by diabetes in 2012 alone. A safe and effective method for long-term management of blood sugar levels is therefore in urgent need.

Currently, the most widely used antidiabetic therapies include insulin, insulin stimulators, and insulin sensitizers, all of which act on insulin, a peptide hormone, or its interacting partners in the insulin signaling pathway that regulates sugar metabolism in the body. These standard anti-diabetic medications are far from fulfilling the immense needs of patients suffering from high blood sugar levels. Insulin, for example, has to be administered by injection or via a continuous intravenous pump. Small-molecule antidiabetic drugs, such as sulphonylurea and metformin, can be administered orally, but they are associated with side effects, such as gastrointestinal irritation and increased burden to the liver. Inconvenience of administration routes and undesirable side effects over extended duration of treatment greatly compromise patients' quality of life and render adherence to the therapeutic regimens rather challenging. As a result, alternative or supplementary means for lowering blood sugar are constantly sought after to satisfy the unmet patient needs.

Herbal medicine and nutritional supplements have long been widely applied by many cultures throughout the world to improve or maintain bodily functions. Traditional Chinese Medicine relies heavily on empirically-tested folk herbal medicines to treat human illnesses. Several herbs from Traditional Chinese Medicine possess hypoglycemic (or blood sugar lowering) effects, including *Cyclocarya paliurus* (wheel wingnut, or Qing qian liu in Chinese), Puerariae lobatae Radix (kudzu root, or Ge gen in Chinese) and Polygonati odorati Rhizoma (Yu zhu in Chinese).

All references described herein are incorporate by reference in their entirety.

BRIEF SUMMARY

The present invention provides a health care composition (or a health-enhancing composition, such as a pharmaceutical composition or a nutritional composition) comprising (including consisting essentially of or consisting of) *Cyclocarya paliurus* leaves and one or more herbs selected from the group consisting of Puerariae lobatae Radix and Polygonati odorati Rhizoma. The invention also provides health care compositions (e.g., a pharmaceutical composition or a nutritional composition) comprising (including consisting essentially of or consisting of) Polygonati odorati Rhizoma and one or more herbs selected from the group consisting of Dendrobii Caulis and Puerariae lobatae Radix, and optionally the composition may further comprise one or more herbs selected from the group consisting of *Cyclocarya paliurus* leaves, *Dioscoreae* Rhizoma, *Poria* and Citri Reticulatae Pericarpium.

In some aspects, provided is an herbal extract composition comprising (including consisting essentially of or consisting of) an extract of *Cyclocarya paliurus* leaves and one or more herbs selected from the group consisting of Puerariae lobatae Radix and Polygonati odorati Rhizoma, a granule comprising the herbal extract composition, methods for preparing the herbal extract composition and the granule thereof, and uses of the herbal extract composition and the granule to reduce blood sugar and to treat or prevent a disease or condition responsive to lowering blood sugar, such as diabetes. Also provided are methods of treating hyperglycemia, hypertension and/or hyperlipidemia.

In some embodiments, provided is an herbal extract composition comprising (including consisting essentially of or consisting of) an extract of *Cyclocarya paliurus* leaves, Puerariae lobatae Radix, and Polygonati odorati Rhizoma. In some embodiments, provided is an herbal extract composition comprising an extract of *Cyclocarya paliurus* leaves, Puerariae lobatae Radix, and Polygonati odorati Rhizoma at relative proportion (by weight) of about 1-98%:1-98%:1-98%, about 10-80%:10-80%:10-80%, about 20-60%:20-60%:20-60%, about 30-50%:30-50%:30-50%, about 30-40%:30-40%:20-30%, about 35%:35%:30%, or about 1:1:1 respectively. In some embodiments, the herbal extract composition contains a total of about less than about 20 ppm (parts per million) of heavy metal (such as mercury).

The herbal extract composition may be prepared for example, by a method comprising the steps of extracting a mixture of *Cyclocarya paliurus* leaves, Puerariae lobatae Radix and Polygonati odorati Rhizoma with water (such as boiling water) to obtain an aqueous extract; concentrating the aqueous extract to obtain a concentrated mixture; obtaining a liquid portion of the concentrated mixture; and optionally spray-drying said liquid portion to produce an herbal extract composition.

Also provided herein are methods of making the herbal extract composition described herein. In some embodiments, there is provided a method for preparing an herbal extract composition comprising an extract of *Cyclocarya paliurus* leaves, Puerariae lobatae Radix and Polygonati odorati Rhizoma, wherein the method comprises: (a) extracting a mixture of *Cyclocarya paliurus* leaves, Puerariae lobatae Radix and Polygonati odorati Rhizoma with water (such as boiling water) to obtain an aqueous extract; (b) concentrating the aqueous extract to obtain a concentrated mixture; (c) obtaining a liquid portion of said concentrated mixture; and optionally (d) spray-drying said liquid portion to produce an herbal extract composition. In some embodiments, there is provided a method for preparing an herbal extract composition comprising an extract of *Cyclocarya paliurus* leaves, Puerariae lobatae Radix and Polygonati odorati Rhizoma, wherein the method comprises: (a) providing a mixture of *Cyclocarya paliurus* leaves, Puerariae lobatae Radix and Polygonati odorati Rhizoma; (b) extracting said mixture with water (such as boiling water) to obtain an aqueous extract; (c) concentrating the aqueous extract to obtain a concentrated mixture; (d) obtaining a liquid portion of said concentrated mixture; and (e) spray-drying said liquid portion to produce an herbal extract composition. In some embodiments, the mixture comprising *Cyclocarya paliurus* leaves, Puerariae lobatae Radix and Polygonati odorati Rhizoma in a relative proportion (by weight) of about 7:7:6, respectively.

In some embodiments according to any one of the methods described herein, the extracting step comprises extracting said mixture with a first portion of water (such as boiling water) for about 1-3 (such as about 2) hours to obtain a first aqueous extract; further extracting said mixture with a second portion of water (such as boiling water) for about 0.5-1.5 (such as about 1) hour to obtain a second aqueous extract; and combining said first aqueous extract and said second aqueous extract to give the aqueous extract. In some embodiments, the first portion of water is about 8-15 (such as about 12) times (by weight) of said mixture of *Cyclocarya paliurus* leaves, Puerariae lobatae Radix and Polygonati odorati Rhizoma, and said second portion of water is about 8-12 (such as about 10) times (by weight) of said mixture of *Cyclocarya paliurus* leaves, Puerariae lobatae Radix and Polygonati odorati Rhizoma. In some embodiments, the method further comprises filtering the aqueous extract through a filter (such as a 150-mesh to 50 mesh, or a 100-mesh filter).

In some embodiments according to any one of the methods described above, the method further comprises a step of removing heavy metal from the herbal mixture. In some embodiments, the step of removing herbal metal can comprise washing the raw materials of *Cyclocarya paliurus* leaves, Puerariae lobatae Radix and Polygonati odorati Rhizoma prior to mixing them together. In some embodiments, the step of removing herbal metal can take place during or after the extraction step. For example, in some embodiments, the extracting step comprises extracting the mixture with a first portion of water (such as boiling water) for about 1-3 (such as about 2) hours to obtain a first aqueous extract, and the first aqueous extract is subject to heavy metal removal. In some embodiments, the extracting step comprises extracting the mixture with a first portion of water (such as boiling water) for about 1-3 (such as about 2) hours to obtain a first aqueous extract; further extracting said mixture with a second portion of water (such as boiling water) for about 0.5-1.5 (such as about 1) hour to obtain a second aqueous extract, and each of the first and second aqueous extract are subject to heavy metal removal separately. In some embodiments, the extracting step comprises extracting the mixture with a first portion of water (such as boiling water) for about 1-3 (such as about 2) hours to obtain a first aqueous extract; further extracting said mixture with a second portion of water (such as boiling water) for about 0.5-1.5 (such as about 1) hour to obtain a second aqueous extract; and combining said first aqueous extract and said second aqueous extract to give the aqueous extract, and the combined extract is subject to heavy metal removal. The heavy metal removal steps comprises, for example, adding potassium carbonate to the aqueous extract and filtering the (first, second, and/or combined) aqueous extract through a filter (such as a 200-40 mesh filter).

In some embodiments according to any one of the methods described above, the concentrating step comprises concentrating the aqueous extract by heating the aqueous extract (for example at about 50~90° C., or about 65~80° C.) under a vacuum (for example under a vacuum of about −0.09~−0.02 MPa, or about −0.08~−0.04 MPa) to obtain a concentrated mixture (for example a concentrated mixture having a relative density of about 1.0-1.2 (such as about 1.1, as measured at about 60° C.)).

In some embodiments according to any one of the methods described above, the liquid portion of the concentrated mixture is obtained after allowing the concentrated mixture to stand at a refrigerated condition (for example at about 0-6° C., such as about 4° C.) for at least 6 hours (such as at least about 10 hours, or about 12 hours).

In some embodiments according to any one of the methods described above, the liquid portion of the concentrated mixture is subject to further heavy metal removal steps comprising optionally adding chitosan to the mixture, allowing the liquid portion to stand for at least 6 hours (such as at least about 10 hours, or about 12 hours), and centrifuging the liquid portion (e.g. at about 4000-8000 rpm for about 15 minutes).

In some embodiments according to any one of the methods described above, the step of spray drying comprise spray-drying said liquid portion in a spray-drying chamber having an in-flow temperature at about 170-250° C. (e.g., about 180-200° C. or 190° C.±10° C.) and an out-flow temperature of about 60-120° C. (such as about 80-100° C. or 90° C.±10° C.) to produce an herbal extract composition.

In some embodiments according to any one of the methods described above, the method further comprises packing and sealing the herbal extract composition in a sterile package.

Also provided herein are herbal extract compositions prepared by a method according to any one of the methods described above.

The herbal extract compositions described above can further be used to make a granule. For example, in some embodiments, there is provided a method for preparing a granule comprising an herbal extract composition and an excipient (such as mannitol), wherein said method comprises: (a) mixing an herbal extract composition comprising an extract of *Cyclocarya paliurus*, Puerariae lobatae Radix, and Polygonati odorati Rhizoma with the excipient (such as mannitol) to obtain a mixture; (b) treating at least a portion of said mixture with an alcoholic solvent (such as 95% alcohol) to obtain a wet granule; and (c) drying the wet granule to obtain a dry granule. In some embodiments, there is provided a method for preparing a granule comprising an herbal extract composition and an excipient (such as mannitol), wherein said method comprises: (a) providing an herbal extract composition comprising an extract of *Cyclocarya paliurus* leaves, Puerariae lobatae Radix, and Polygonati odorati Rhizoma; (b) mixing said herbal extract composition with the excipient (such as mannitol) to obtain a mixture; (c) treating at least a portion of said mixture with an alcoholic solvent (such as 95% alcohol) to obtain a wet granule; and (d) drying the wet granule to obtain a dry granule.

In some embodiments, the herbal extract is made by any one of the methods described herein. Thus, for example, in some embodiments, there is provided a method for method for preparing a granule comprising an herbal extract composition and an excipient (such as mannitol), wherein said method comprises: (a) mixing an herbal extract composition comprising an extract of *Cyclocarya paliurus* leaves, Puerariae lobatae Radix, and Polygonati odorati Rhizoma with the excipient (such as mannitol) to obtain a mixture; (b) treating at least a portion of said mixture with an alcoholic solvent (such as 95% alcohol) to obtain a wet granule; and (c) drying the wet granule to obtain a dry granule, wherein the herbal extract composition is prepared by a method comprising: (i) extracting a mixture of *Cyclocarya paliurus* leaves, Puerariae lobatae Radix and Polygonati odorati Rhizoma with water (such as boiling water) to obtain an aqueous extract; (ii) concentrating the aqueous extract to obtain a concentrated mixture; (iii) obtaining a liquid portion of said concentrated mixture; and optionally (iv) spray-drying said liquid portion to produce an herbal extract composition. In some embodiments, there is provided a method for method for preparing a granule comprising an herbal extract composition and an excipient (such as mannitol), wherein said method comprises: (a) extracting a mixture of *Cyclocarya paliurus* leaves, Puerariae lobatae Radix and Polygonati odorati Rhizoma with water (such as boiling water) to obtain an aqueous extract; (b) concentrating the aqueous extract to obtain a concentrated mixture; (c) obtaining a liquid portion of said concentrated mixture; and optionally (d) spray-drying said liquid portion to produce an herbal extract composition; (e) mixing the herbal extract composition with the excipient (such as mannitol) to obtain a mixture; (f) treating at least a portion of said mixture with an alcoholic solvent (such as 95% alcohol) to obtain a wet granule; and (g) drying the wet granule to obtain a dry granule.

In some embodiments according to any one of the methods of preparing a granule described above, the method comprises weighing a predetermined amount of the herbal extract composition and a predetermined amount of the excipient (such as mannitol) prior to mixing the components together. In some embodiments, the components are mixed for about 2-10 minutes (for example about 10 minutes) to obtain a uniform mixture.

In some embodiments according to any one of the methods of preparing a granule described above, the wet granules are further sieved (for example through a 10-mesh to 20-mesh sieve) prior to the drying step.

In some embodiments according to any one of the methods of preparing a granule described above, the drying of the wet granules comprises drying the wet granules at an elevated temperature (for example at about 40-90° C., or about 65-75° C. or 70° C.±5° C.) to obtain a dry granule (for example a dry granule contains less than about 5% water). In some embodiments, the dry granules are further sieved (for example through a 10-mesh or 20-mesh sieve). In some embodiments, the dry granules are sieved through a sieve of about 10-mesh and a sieve of about 100-mesh to obtain the dry granules having a particle size between about 100 mesh and about 10 mesh. In some embodiments the dry granules are further mixed for about 10-30 minutes to obtain a second mixture, wherein said second mixture is a uniform mixture.

In some embodiments according to any one of the methods of preparing a granule described above, the method further comprises polishing the gel capsule, packaging and/or testing for quality control.

Also provided is a granule (or granules) comprising an extract of *Cyclocarya paliurus* leaves, Puerariae lobatae Radix and Polygonati odorati Rhizoma produced by any one of the methods described above.

Further provided are nutritional compositions or pharmaceutical compositions comprising any one of the herbal extract compositions or granules described above. In some embodiments, the nutritional composition or pharmaceutical composition further comprises a neutraceutically or pharmaceutically acceptable carrier. The compositions are useful, for example, for lowering blood sugar, promoting general health, and improving quality of life.

In some embodiments, there is provided a method of lowering blood sugar in an individual (such as a human individual), comprising administering to the individual an effective amount of any one of the herbal extract composition or granules described above.

In some embodiments, there is provided a method of providing nutritional supplement to an individual (such as a human individual), comprising administering to the individual an effective amount of any one of the herbal extract composition or granules described above.

In some embodiments, there is provided a method of treating a disease or condition responsive to lowering of blood sugar in an individual (such as a human individual), comprising administering to the individual an effective amount of any one of the herbal extract composition or granules described above. In some embodiments, the disease is diabetes.

In some embodiments, there is provided a use of any one of the herbal extracts described above for the manufacture of medicament for lowering blood sugar, treating a disease, or providing nutritional supplement.

BRIEF DESCRIPTION OF THE DRAWINGS

FIG. 1 shows the names in Chinese characters for some of the Chinese herbal medicines described herein.

DETAILED DESCRIPTIONS

Figure 2:
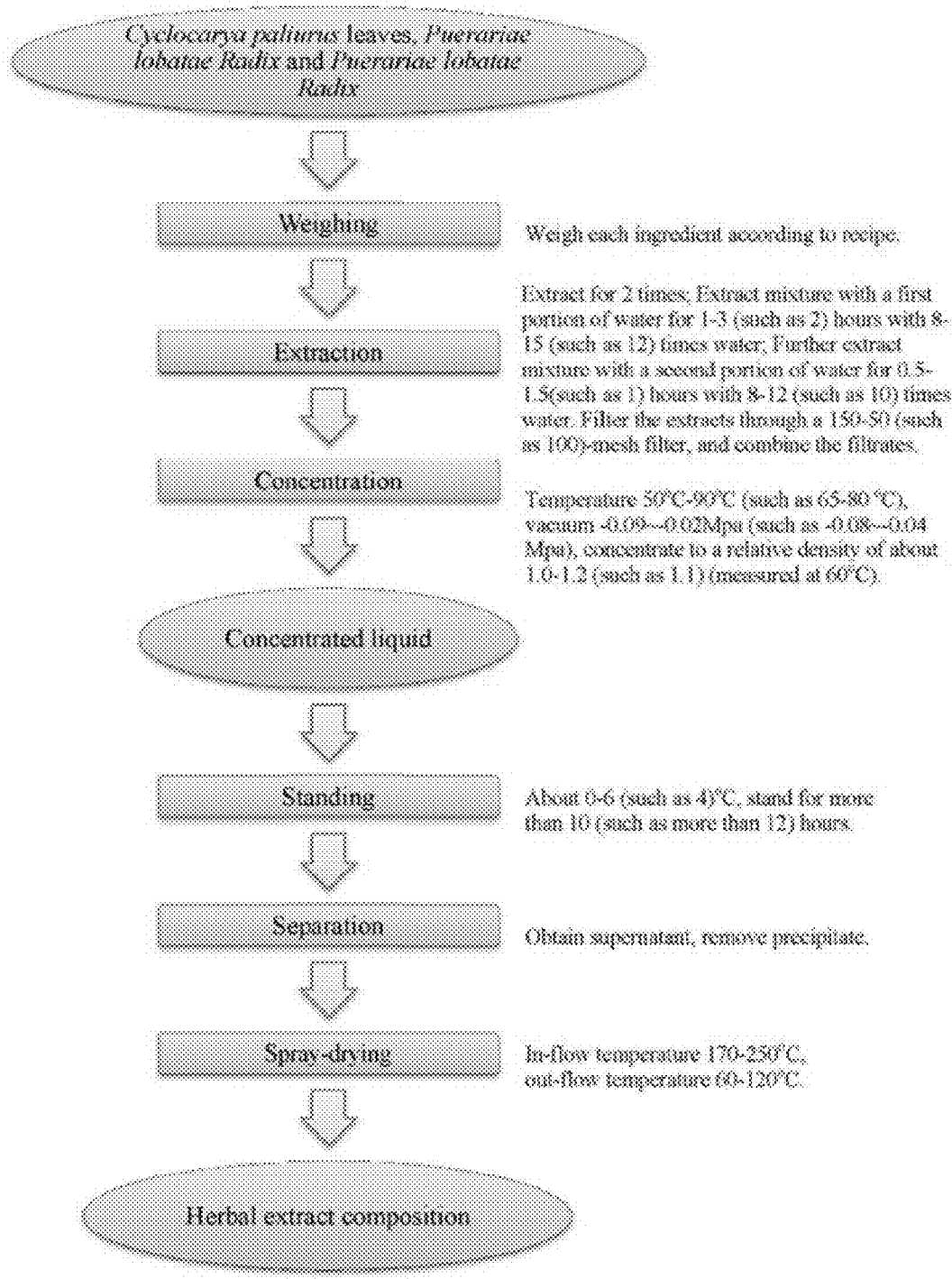
FIG. 2 shows a schematic flow chart of an exemplary embodiment of a method for preparing an herbal extract composition comprising (including consisting essentially of or consisting of) an extract of *Cyclocarya paliurus* leaves, Puerariae lobatae Radix and Polygonati odorati Rhizoma.

The present invention provides a health care composition (or a health-enhancing composition, e.g., a pharmaceutical composition or a nutritional composition) comprising (including consisting essentially of or consisting of) *Cyclocarya paliurus* leaves and one or two herbs selected from the group consisting of Puerariae lobatae Radix and Polygonati odorati Rhizoma. Also provided are methods of using any of the compositions in lowering blood sugar, treating a disease or condition (e.g., diabetes, hyperglycemia, hypertension or hyperlipidemia), or providing nutritional supplement, to an individual in need thereof. Further provided are methods and processes for preparing or manufacturing the compositions described herein.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X".

Unless otherwise noted, technical terms are used according to conventional usage.

The compositions and methods of the present invention may comprise, consist of, or consist essentially of the essential elements and limitations of the invention described herein, as well as any additional or optional ingredients, components, or limitations described herein or otherwise useful.

It is understood that aspects and embodiments of the invention described herein include "comprising", "consisting of", and "consisting essentially of" aspects and embodiments. For example, for all compositions described herein, and all methods using or making a composition described herein, the compositions can either comprise the listed components or steps, or can "consist essentially of" the listed components or steps. A composition consisting essentially of a list of components contains at least 60% (e.g., by weight) of the listed components. In some embodiments, a composition consisting essentially of a list of components contains at least 65%, 70%, 75%, 80%, 85%, 90% or 95% (e.g., by weight) of the listed components. In some embodiments, a composition consisting essentially of a list of components contains at least 95%, 96%, 97%, 98% or 99% (e.g., by weight) of the listed components. In some embodiments, a composition consisting essentially of a list of components contains about 99%, about 99.5% or about 99.9% (e.g., by weight) of the listed components. For example, in a pharmaceutical composition consisting essentially of a list of herbal components (e.g., *Cyclocarya paliurus* leaves, Puerariae lobatae Radix and Polygonati odorati Rhizoma), the listed herbal components account for at least 60% (e.g., by weight) of all of the active ingredients. In some embodiments, the pharmaceutical composition contains at least 70%, 75%, 85%, 90%, 95%, or 99% (by weight) of list of herbal components (e.g., *Cyclocarya paliurus* leaves, Puerariae lobatae Radix and Polygonati odorati Rhizoma). In some embodiments, the pharmaceutical composition contains about 99%, about 99.5% or about 99.9% (by weight) of list of herbal components (e.g., *Cyclocarya paliurus* leaves, Puerariae lobatae Radix and Polygonati odorati Rhizoma).

As used herein, a composition comprising an herb (e.g., *Cyclocarya paliurus* leaves) means the composition includes (inclusive or open-ended) the herb in its raw form or processed form, for example, crushed and sieved parts or particles, or extracts of the herb. When a percentage (or relative amount) of an herb is stated for a composition obtained by processing a mixture of more than one herbs, the percentage or relative amount indicates the proportion of the herb in the mixture before the mixture is processed. For example, when an herbal extract composition obtained by extracting a mixture of *Cyclocarya paliurus* leaves and other herbs is stated to comprise about 50% (by weight) of *Cyclocarya paliurus* leaves, the mixture comprises about 50% (by weight) of *Cyclocarya paliurus* leaves before extraction.

Health Care Compositions

*Cyclocarya paliurus* is also known as wheel wingnut, sweet tea tree, or in Traditional Chinese Medicine Qing qian liu. A native deciduous tree of China and the sole species in the genus of flowering plants named *Cyclocarya* in the family Juglandaceae, *Cyclocarya paliurus* is found in the foggy high-mountain regions in southern China. The leaves of *Cyclocarya paliurus* are particularly suitable for use in nutritional and pharmaceutical compositions for human consumption, because the leaves have a sweet flavor and contain many chemical constituents with health benefits, including proteins, polysaccharides, triterpenoids, flavonoids, and phenolic compounds. In the present invention, the term "*Cyclocarya paliurus*" refers to the plant or any part of the plant, including but not limited to its leaves, bark, stem, root, buds and flowers. Additionally, the plant parts of *Cyclocarya paliurus* can be young or old, fresh or dried, raw or processed. Indications and properties of *Cyclocarya paliurus* leaves as a traditional Chinese medicine include the following: slightly bitter, pungent, neutral; acts to tonify spleen and resolve dampness, clear heat and soothe viscera, relieve Qi stagnancy in liver, nourish kidney Yin; effective for relieving obesity due to non-invigorating spleen, phlegm turbidity, preference in fatty, sweet, and heavy-taste food, laziness to move, food retention, liver depression and Qi stagnation.

Puerariae lobatae Radix is also known as Radix Puerariae, Radix Puerariae lobatae, kudzu root, or in Traditional Chinese Medicine Ge gen. The herb is prepared from the root of a perennial, fast-growing vine species named *Pueraria lobata* (kudzu or Japanese arrowroot), particularly subspecies *Liane Pueraria lobata* (Ohwi) or *Pueraria thomsonii* Benth, in the pea family Fabaceae, which can be found in the wild or cultivated in southern China. The plant contains a number of bioactive substances, such as isoflavones, which have found versatile uses for treating alcoholism, heart and vascular problems, infections, and diabetes. Puerariae lobatae Radix is therefore considered as one of the 50 fundamental herbs in Traditional Chinese Medicine. Puerariae lobatae Radix is odorless, has a slight bitter sweet taste, and can appear as unprocessed chunks with profuse powder inside, or roasted chunks. In the present invention, the term "Puerariae lobatae Radix" refers to the root of *Pueraria lobata*, in fresh or dried, raw or processed (such as roasted) conditions. Indications and properties of Puerariae lobatae Radix as a traditional Chinese medicine include but are not limited to the following: sweet, pungent, cool; entering lung and stomach meridians; acts to release the muscles, cure fever, discharge measles, promote production of fluid and relieve thirst, ascend Yang to stop diarrhea; applicable for treating high fever of exterior syndromes, muscle pain of the upper back and neck, measles with incomplete eruption, thirst due to warm diseases, Yin deficiency converting into dryness, diarrhea or dysentery due to heat, and diarrhea due to spleen deficiency.

Polygonati odorati Rhizoma is also known as Rhizoma Polygonati odorati, fragrant Solomonseal rhizome, or in Traditional Chinese Medicine Yu zhu. The herb is prepared from the rhizome, or the subterranean stem including roots, of a flowering perennial plant named *Polygonatum odoratum* (angular Solomon's seal, or scented Solomon's seal) in the family Asparagaceae, which is widely cultivated in moist, shaded regions across Asia and Europe. Polygonati odorati Rhizoma has a sweet flavor and a sticky texture, which are amenable for use in food and herbal medicine. Active substances from the extracts of Polygonati odorati Rhizoma include saponin, flavonoids and steroidal glycosides, which have been shown experimentally to reduce blood glucose and improve insulin resistance in animal models. In the present invention, the term "Polygonati odorati Rhizoma" refers to the rhizome of any of various subspecies of the plant *Polygonatum odoratum*, and such rhizome can be in raw or processed, fresh or dried conditions. Indications and properties of *Cyclocarya paliurus* leaves as a traditional Chinese medicine include the following: having functions of nourishing Yin, moistening dryness, clearing heat, producing fluids, and relieving cough; useful as nourishing medicine; capable of treating Yin deficiency due to heat syndromes, empty heat and dry cough, heart disease, diabetes, and tuberculosis.

The invention provides a health care composition (or a health-enhancing composition, e.g., a pharmaceutical composition or a nutritional composition) comprising (including consisting essentially of or consisting of) *Cyclocarya paliurus* leaves and one or more herbs selected from the group consisting of Puerariae lobatae Radix and Polygonati odorati Rhizoma. In some instances, the composition comprises (including consists essentially of or consists of) parts or particles obtained by mechanically processing the herbs. For example, the composition may comprise crushed parts of the herbs mixed together in packet (e.g., a tea bag). In some instances, the composition comprises (including consists essentially of or consists of) substances extracted from *Cyclocarya paliurus* leaves and the other herbs, for example, by using a method described herein for preparing an herbal extract composition. The health care composition disclosed herein comprising the herbs may provide synergistic effect in lowering blood sugar, while avoiding excessive toxicity often associated with long-term usage of Traditional Chinese Medicine due to factors such as heavy metal contamination and impurities.

In some embodiments, the health care composition comprises (including consists essentially of or consists of) *Cyclocarya paliurus* leaves and one herb selected from the group consisting of Puerariae lobatae Radix and Polygonati odorati Rhizoma. In some embodiments, the health care composition comprises (including consists essentially of or consists of) *Cyclocarya paliurus* leaves, Puerariae lobatae Radix and Polygonati odorati Rhizoma. The composition may further comprise one or more other herbs.

In some preferred embodiments, the health care composition (e.g., a pharmaceutical composition or a nutritional composition) comprises (including consists essentially of or consists of) *Cyclocarya paliurus* leaves and Puerariae lobatae Radix. In some embodiments, the composition comprises about 10-90% (w) *Cyclocarya paliurus* leaves and about 10-90% (w) Puerariae lobatae Radix. In some embodiments, the composition comprises about 20-80% (w) *Cyclocarya paliurus* leaves and about 20-80% (w) Puerariae lobatae Radix. In some embodiments, the composition comprises about 30-70% (w) *Cyclocarya paliurus* leaves and about 30-70% (w) Puerariae lobatae Radix. In some embodiments, the health care composition consists essentially of *Cyclocarya paliurus* leaves and Puerariae lobatae Radix. In some embodiments, the health care composition consists essentially of *Cyclocarya paliurus* leaves and Puerariae lobatae Radix, wherein the *Cyclocarya paliurus* leaves and Puerariae lobatae Radix have a relative proportion (by weight) of about 1:1. In some embodiments, the composition consists of *Cyclocarya paliurus* leaves and Puerariae lobatae Radix at a relative proportion (by weight) of about 1:1. In some embodiments, the composition further comprises one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 1-98% (w) *Cyclocarya paliurus* leaves, about 1-98% (w) Puerariae lobatae Radix and about 1-98% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 10-80% (w) *Cyclocarya paliurus* leaves, about 10-80% (w) Puerariae lobatae Radix and about 10-80% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 20-60% (w) *Cyclocarya paliurus* leaves, about 20-60% (w) Puerariae lobatae Radix and about 20-60% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 20-40% (w) *Cyclocarya paliurus* leaves, about 20-40% (w) Puerariae lobatae Radix and about 20-40% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 80% (w) *Cyclocarya paliurus* leaves, about 10% (w) Puerariae lobatae Radix and about 10% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 20% (w) *Cyclocarya paliurus* leaves, about 50% (w) Puerariae lobatae Radix and about 30% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 37.5% (w) *Cyclocarya paliurus* leaves, about 37.5% (w) Puerariae lobatae Radix and about 25% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments, the composition comprises about 60% (w) *Cyclocarya paliurus* leaves, about 20% (w) Puerariae lobatae Radix and about 20% (w) of one or more herbs selected from the group consisting of Citri Reticulatae Pericarpium, *Dioscoreae* Rhizoma, Polygonati odorati Rhizoma, *Poria*, and Dendrobii Caulis. In some embodiments of any of the compositions, the composition further comprises one or more herbs selected from the group consisting of Mori Folium, Lycii Fructus, Polygonati Rhizoma, Laminariae Thallus/Eckloniae Thallus, Mume Fructus, Mori Cortex, *Ginseng* Radix et Rhizoma, *Notoginseng* Radix et Rhizoma, *Ligustri lucidi* Fructus, Corni Fructus, Chuanxiong Rhizoma, Atractylodis Rhizoma, Scrophulariae Radix, Rehmanniae Radix, Paeoniae Radix alba, *Angelicae sinensis* Radix, Rhodiolae Crenulatae Radix et Rhizoma, *Panacis Quinquefolii* Radix, Aloe, *Schisandrae chinensis* Fructus, Ophiopogonis Radix, Prepared Rhubarb, Anemarrhenae Rhizoma, Tribuli Fructus, *Ginkgo* Folium, Astragali Radix, *Gynostemma pentaphyllum*, Balsam pear, *Fagopyrum tataricum*, Pumpkin, Konjac, Celery, Corn Stigma, *Tremella, Hericium erinaceus*, and Garlic.

In some preferred embodiments, the health care composition (e.g., a pharmaceutical composition or a nutritional composition) comprises (including consists essentially of or consists of) *Cyclocarya paliurus* leaves, Puerariae lobatae Radix and Polygonati odorati Rhizoma. In some embodiments, the composition comprises about 1-98% (w) *Cyclo-*

*carya paliurus* leaves, about 1-98% (w) Puerariae lobatae Radix and about 1-98% (w) Polygonati odorati Rhizoma. In some embodiments, the composition comprises about 10-80% (w) *Cyclocarya paliurus* leaves, about 10-80% (w) Puerariae lobatae Radix and about 10-80% (w) Polygonati odorati Rhizoma. In some embodiments, the composition comprises about 20-60% (w) *Cyclocarya paliurus* leaves, about 20-60% (w) Puerariae lobatae Radix and about 20-60% (w) Polygonati odorati Rhizoma. In some embodiments, the composition comprises about 30-50% (w) *Cyclocarya paliurus* leaves, about 30-50% (w) Puerariae lobatae Radix and about 30-50% (w) Polygonati odorati Rhizoma. In some embodiments, the composition comprises about 30-40% (w) *Cyclocarya paliurus* leaves, about 30-40% (w) Puerariae lobatae Radix and about 20-30% (w) Polygonati odorati Rhizoma. In some embodiments, the composition comprises about 35% (w) *Cyclocarya paliurus* leaves, about 35% (w) Puerariae lobatae Radix and about 30% (w) Polygonati odorati Rhizoma. In some embodiments, the health care composition consists essentially of *Cyclocarya paliurus* leaves, Puerariae lobatae Radix and Polygonati odorati Rhizoma. In some embodiments, the health care composition consists essentially of *Cyclocarya paliurus* leaves, Puerariae lobatae Radix and Polygonati odorati Rhizoma, wherein the *Cyclocarya paliurus* leaves, Puerariae lobatae Radix and Polygonati odorati Rhizoma have a relative proportion (by weight) of about 1-98%:1-98%:1-98%, about 10-80%:10-80%:10-80%, about 20-60%:20-60%:20-60%, about 30-50%:30-50%:30-50%, about 30-40%:30-40%:20-30%, about 35%:35%:30%, or about 1:1:1, respectively. In some embodiments, the composition consists of *Cyclocarya paliurus* leaves, Puerariae lobatae Radix and Puerariae lobatae Radix at a relative proportion (by weight) of about 35%:35%:30%, or about 1:1:1, respectively. In some embodiments of any of the compositions, the composition further comprises one or more herbs selected from the group consisting of Mori Folium, Lycii Fructus, Polygonati Rhizoma, Laminariae Thallus/Eckloniae Thallus, Mume Fructus, Mori Cortex, Ginseng Radix et Rhizoma, *Notoginseng* Radix et Rhizoma, *Ligustri* lucidi Fructus, Corni Fructus, Chuanxiong Rhizoma, Atractylodis Rhizoma, Scrophulariae Radix, Rehmanniae Radix, Paeoniae Radix alba, *Angelicae sinensis* Radix, Rhodiolae Crenulatae Radix et Rhizoma, *Panacis Quinquefolii* Radix, Aloe, *Schisandrae chinensis* Fructus, Ophiopogonis Radix, Prepared Rhubarb, Anemarrhenae Rhizoma, Tribuli Fructus, *Ginkgo* Folium, Astragali Radix, *Gynostemma pentaphyllum*, Balsam pear, *Fagopyrum tataricum*, Pumpkin, Konjac, Celery, Corn Stigma, *Tremella, Hericium erinaceus*, and Garlic.

The invention also provides other health care compositions (e.g., a pharmaceutical composition or a nutritional composition) comprising (including consisting essentially of or consisting of) Polygonati odorati Rhizoma and one or more herbs selected from the group consisting of Dendrobii Caulis and Puerariae lobatae Radix, and optionally the composition may further comprise one or more herbs selected from the group consisting of *Cyclocarya paliurus* leaves, *Dioscoreae* Rhizoma, *Poria* and Citri Reticulatae Pericarpium. The composition may be an oral formulation such as a tablet, a capsule, a granule, a powder, an effervescent tablet, or an herbal tea formulation, useful in lowering blood sugar, treating a disease or condition (e.g., diabetes, hyperglycemia, hypertension or hyperlipidemia), or providing nutritional supplement, to an individual in need thereof. These compositions can be made using methods and processes known in the art and those described herein.

In one embodiment, the health care composition (e.g., a pharmaceutical composition or a nutritional composition) comprises (including consists essentially of or consists of) Puerariae lobatae Radix and Polygonati odorati Rhizoma. In some embodiments, the composition comprises about 1-99% (w) Puerariae lobatae Radix and about 1-99% (w) Polygonati odorati Rhizoma. In some embodiments, the composition comprises about 20-80% (w) Puerariae lobatae Radix and about 20-80% (w) Polygonati odorati Rhizoma. In some embodiments, the composition comprises about 30-70% (w) Puerariae lobatae Radix and about 30-70% (w) Polygonati odorati Rhizoma. In some embodiments, the composition comprises about 40-60% (w) Puerariae lobatae Radix and about 40-60% (w) Polygonati odorati Rhizoma. In some embodiments, the health care composition consists essentially of Puerariae lobatae Radix and Polygonati odorati Rhizoma. In some embodiments, the composition further comprises one or more herbs selected from the group consisting of Citri Reticulatae Pericarpium, *Dioscoreae* Rhizoma, *Cyclocarya paliurus* leaves, *Poria*, and Dendrobii Caulis. In some embodiments, the composition comprises about 1-98% (w) Puerariae lobatae Radix, about 1-98% (w) Polygonati odorati Rhizoma and about 1-98% (w) of one or more herbs selected from the group consisting of Citri Reticulatae Pericarpium, *Dioscoreae* Rhizoma, *Cyclocarya paliurus* leaves, *Poria*, and Dendrobii Caulis. In some embodiments, the composition comprises about 10-80% (w) Puerariae lobatae Radix, about 10-80% (w) Polygonati odorati Rhizoma and about 10-80% (w) of one or more herbs selected from the group consisting of Citri Reticulatae Pericarpium, *Dioscoreae* Rhizoma, *Cyclocarya paliurus* leaves, *Poria*, and Dendrobii Caulis. In some embodiments, the composition comprises about 20-60% (w) Puerariae lobatae Radix, about 20-60% (w) Polygonati odorati Rhizoma and about 20-60% (w) of one or more herbs selected from the group consisting of Citri Reticulatae Pericarpium, *Dioscoreae* Rhizoma, *Cyclocarya paliurus* leaves, *Poria*, and Dendrobii Caulis. In some embodiments, the composition comprises about 35% (w) Puerariae lobatae Radix, about 35% (w) Polygonati odorati Rhizoma and about 30% (w) of one or more herbs selected from the group consisting of Citri Reticulatae Pericarpium, *Dioscoreae* Rhizoma, *Cyclocarya paliurus* leaves, *Poria*, and Dendrobii Caulis. In some embodiments of any of the compositions, the composition further comprises one or more herbs selected from the group consisting of Mori Folium, Lycii Fructus, Polygonati Rhizoma, Laminariae Thallus/Eckloniae Thallus, Mume Fructus, Mori Cortex, Ginseng Radix et Rhizoma, *Notoginseng* Radix et Rhizoma, *Ligustri lucidi* Fructus, Corni Fructus, Chuanxiong Rhizoma, Atractylodis Rhizoma, Scrophulariae Radix, Rehmanniae Radix, Paeoniae Radix alba, *Angelicae sinensis* Radix, Rhodiolae Crenulatae Radix et Rhizoma, *Panacis Quinquefolii* Radix, Aloe, *Schisandrae chinensis* Fructus, Ophiopogonis Radix, Prepared Rhubarb, Anemarrhenae Rhizoma, Tribuli Fructus, *Ginkgo* Folium, Astragali Radix, *Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition comprises (including consists essentially of or consists of) Dendrobii Caulis and Polygonati odorati Rhizoma. In some embodiments, the composition comprises about 1-99% (w) Dendrobii Caulis and about 1-99% (w) Polygonati odorati Rhizoma. In some embodiments, the composition comprises about 20-80% (w) Dendrobii Caulis and about 20-80% (w) Polygonati odorati Rhizoma. In some embodiments, the composition comprises about 30-70% (w) Dendrobii Caulis and about 30-70% (w) Polygonati odorati Rhizoma. In some embodiments, the composition comprises about 40-60% (w) Dendrobii Caulis and about 40-60% (w) Polygonati odorati Rhizoma. In some embodiments, the health care composition consists essentially of Dendrobii Caulis and Polygonati odorati Rhizoma. In some embodiments, the composition further comprises one or more herbs selected from the group consisting of Citri Reticulatae Pericarpium, *Dioscoreae* Rhizoma, *Cyclocarya paliurus* leaves, *Poria*, and Puerariae lobatae Radix. In some embodiments, the composition comprises about 1-98% (w) Dendrobii Caulis, about 1-98% (w) Polygonati odorati Rhizoma and about 1-98% (w) of one or more herbs selected from the group consisting of Citri Reticulatae Pericarpium, *Dioscoreae* Rhizoma, *Cyclocarya paliurus* leaves, *Poria*, and Puerariae lobatae Radix. In some embodiments, the composition comprises about 10-80% (w) Dendrobii Caulis, about 10-80% (w) Polygonati odorati Rhizoma and about 10-80% (w) of one or more herbs selected from the group consisting of Citri Reticulatae Pericarpium, *Dioscoreae* Rhizoma, *Cyclocarya paliurus* leaves, *Poria*, and Puerariae lobatae Radix. In some embodiments, the composition comprises about 20-60% (w) Dendrobii Caulis, about 20-60% (w) Polygonati odorati Rhizoma and about 20-60% (w) of one or more herbs selected from the group consisting of Citri Reticulatae Pericarpium, *Dioscoreae* Rhizoma, *Cyclocarya paliurus* leaves, *Poria*, and Puerariae lobatae Radix. In some embodiments, the composition comprises about 35% (w) Dendrobii Caulis, about 35% (w) Polygonati odorati Rhizoma and about 30% (w) of one or more herbs selected from the group consisting of Citri Reticulatae Pericarpium, *Dioscoreae* Rhizoma, *Cyclocarya paliurus* leaves, *Poria*, and Puerariae lobatae Radix. In some embodiments of any of the compositions, the composition further comprises one or more herbs selected from the group consisting of Mori Folium, Lycii Fructus, Polygonati Rhizoma, Laminariae Thallus/Eckloniae Thallus, Mume Fructus, Mori Cortex, *Ginseng* Radix et Rhizoma, *Notoginseng* Radix et Rhizoma, *Ligustri lucidi* Fructus, Corni Fructus, Chuanxiong Rhizoma, Atractylodis Rhizoma, Scrophulariae Radix, Rehmanniae Radix, Paeoniae Radix alba, *Angelicae sinensis* Radix, Rhodiolae Crenulatae Radix et Rhizoma, *Panacis Quinquefolii* Radix, Aloe, *Schisandrae chinensis* Fructus, Ophiopogonis Radix, Prepared Rhubarb, Anemarrhenae Rhizoma, Tribuli Fructus, *Ginkgo* Folium, Astragali Radix, *Gynostemma pentaphyllum*, Balsam pear, *Fagopyrum tataricum*, Pumpkin, Konjac, Celery, Corn Stigma, *Tremella, Hericium erinaceus*, and Garlic.

The health care composition may be an oral formulation such as a tablet, a capsule, a granule, a powder, an effervescent tablet, or an herbal tea formulation. The health care composition (such as a pharmaceutical composition or a nutritional composition) may further comprise one or more excipients. Examples of pharmaceutically acceptable excipient include but are not limited to pregelatinized starch, β-cyclodextrin, maltodextrin, Carbopol, microcrystalline cellulose, hydroxypropylmethylcellulose, low-substituted hydroxypropylcellulose, polyethylene glycol (PEG), sodium carboxymethyl cellulose, methylcellulose, ethylcellulose, mannitol, cross-linked sodium carboxymethyl cellulose, lactose, polyvinylpyrrolidone (PVP), magnesium stearate, talc, silica powder, aspartame, sodium bicarbonate, and sodium carbonate.

The health care compositions comprising the herbs (e.g., a Chinese herbal medicine) described herein may be prepared by methods known in the art, and methods described herein. For example, an herbal tea composition comprising one or more of the herbs described herein can be prepared by crushing and sieving the herbs, and packaging in a packet (e.g., a tea bag). A granule composition can be prepared by extracting the herbs with a solvent (e.g., hot water) and converting the extracts into granules by using auxiliary agents or excipients such as β-cyclodextrin, microcrystalline cellulose, calcium hydrogen phosphate, or mannitol. A gel capsule composition can be manufactured by enclosure of a granule composition in a gel capsule. An herbal extract composition can be prepared by extracting the herbs, and removing impurities, for example, by filtration and centrifugation. Powders, oral tablets and effervescent tablets can be prepared using the herbal extracts and appropriate auxiliary materials by processes known in the art.

Herbal Extract Compositions and Method of Preparation

One aspect of the invention provides an herbal extract composition comprising (including consisting essentially of or consisting of) an extract from a mixture of herbs known in Traditional Chinese Medicine, for example, *Cyclocarya paliurus* leaves, Puerariae lobatae Radix and Polygonati odorati Rhizoma. Further provided is a method for preparing the herbal extract composition. Each of the three herbs is known to have certain beneficial health effects, including hypoglycemic effects (e.g. reduction of blood sugar levels). The herbal extract composition disclosed herein comprising extracts from all three herbs may provide synergistic effect in lowering blood sugar, while avoiding excessive toxicity often associated with long-term usage of Traditional Chinese Medicine due to factors such as heavy metal contamination and impurities. The herbal extract composition and its derivatives in the form of a granule, a pharmaceutical composition, or a nutritional composition, used alone or in conjunction with standard anti-diabetic medication, can be a sustainable, cost-effective, and useful therapy for patients with diabetes, or people with other health conditions in need of lowering their blood sugar.

The present invention provides a method for preparing an herbal extract composition comprising (including consisting essentially of or consisting of) an extract of *Cyclocarya paliurus* leaves, Puerariae lobatae Radix and Polygonati odorati Rhizoma. The method comprises the steps of:

i) providing a mixture of *Cyclocarya paliurus* leaves, Puerariae lobatae Radix and Polygonati odorati Rhizoma;

ii) extracting said mixture with water (e.g., boiling water) to obtain an aqueous extract;

iii) concentrating the aqueous extract to obtain a concentrated mixture;

iv) obtaining a liquid portion of said concentrated mixture; and v) drying (e.g., spray-drying) said liquid portion to produce the herbal extract composition.

The present invention provides an herbal extract composition prepared by the method described herein. The present invention further provides an herbal extract composition comprising an extract of *Cyclocarya paliurus*, Puerariae lobatae Radix and Polygonati odorati Rhizoma. In some embodiments, the herbal extract composition consists essentially of or consists of an extract from a mixture comprising (including consisting essentially of or consisting of) *Cyclocarya paliurus* leaves, Puerariae lobatae Radix and Polygonati odorati Rhizoma.

The relative proportion of *Cyclocarya paliurus* leaves, Puerariae lobatae Radix and Polygonati odorati Rhizoma in the herbal extract composition can be important for achieving optimal health benefits. In some embodiments, in the mixture of the three herbal components used to prepare the herbal extract composition, the relative ratio (by weight) of Cyclocarya paliurus leaves to Puerariae lobatae Radix is about 1:4 to about 1:3, about 1:3 to about 1:2, about 1:3 to about 1:1, about 1:1 to about 2:1, about 2:1 to about 3:1, about 3:1 to about 4:1, about 1.2:1 to about 1:1.2, or preferably about 1:1. In some embodiments, the relative ratio (by weight) of Cyclocarya paliurus leaves to Polygonati odorati Rhizoma is about 1:4 to about 1:3, about 1:3 to about 1:2, about 1:3 to about 1:1, about 1:1 to about 2:1, about 2:1 to about 3:1, about 3:1 to about 4:1, or preferably about 7:6. In an exemplary embodiment, the herbal extract composition comprises (including consists essentially of or consists of) an extract from a mixture of Cyclocarya paliurus leaves, Puerariae lobatae Radix and Polygonati odorati Rhizoma, wherein the mixture comprises (including consists essentially of or consists of) Cyclocarya paliurus leaves, Puerariae lobatae Radix and Polygonati odorati Rhizoma in a relative proportion (by weight) of about 1-98%:1-98%:1-98%, about 10-80%:10-80%:10-80%, about 20-60%:20-60%:20-60%, about 30-50%:30-50%:30-50%, about 30-40%:30-40%:20-30%, about 35%:35%:30%, or about 1:1:1, respectively.

In some embodiments, in the mixture of the three herbal components used to prepare the herbal extract composition, the percentage by weight of Cyclocarya paliurus leaves is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 30-45%, 30-40%, or preferably about 35%. In some embodiments, the percentage by weight of Puerariae lobatae Radix is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 30-45%, 30-40%, or preferably about 35%. In some embodiments, the percentage by weight of Polygonati odorati Rhizoma is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 20-30%, or preferably about 30%. In an exemplary embodiment, the herbal extract composition comprises (including consists essentially of or consists of) an extract from an herbal mixture, wherein the mixture comprises (including consists essentially of or consists of) about 30-30% by weight of Cyclocarya paliurus leaves, about 30-40% by weight of Puerariae lobatae Radix, and about 20-30% by weight of Polygonati odorati Rhizoma. In an exemplary embodiment, the herbal extract composition comprises (including consists essentially of or consists of) an extract from an herbal mixture, wherein the mixture comprises (including consists essentially of or consists of) about 35% by weight of Cyclocarya paliurus leaves, about 35% by weight of Puerariae lobatae Radix, and about 30% by weight of Polygonati odorati Rhizoma.

In a preferred embodiment of the present invention, in step i) of the method for preparing the herbal extract composition, for each about 7 portions (by weight) of Cyclocarya paliurus leaves, about 7 portions (by weight) of Puerariae lobatae Radix, and about 6 portions (by weight) of Polygonati odorati Rhizoma are provided. In a particular embodiment, about 3500 grams of Cyclocarya paliurus leaves, about 3500 grams of Puerariae lobatae Radix, and about 3000 grams of Polygonati odorati Rhizoma are provided. The relative proportion of individual components within the composition can be reasonably adjusted by persons skilled in the art according to actual production situation. In some embodiments, the mixture of crude herbs comprising (including consisting essentially of or consisting of) Cyclocarya paliurus leaves, Puerariae lobatae Radix, and Polygonati odorati Rhizoma are optionally washed with potable water for multiple times (e.g. 3 times), or washed under running tap water for about any of 1 minute, 2 minutes, 5 minutes, or more than 5 minutes, to remove impurities, which may contain toxic substances and/or heavy metals. In some embodiments, potassium carbonate can optionally be added to the washed mixture of herbs, which may further reduce heavy metal contents in the herbal extract composition.

The extraction step ii) in the method for preparing the herbal extract composition can comprise one aqueous extraction step, two aqueous extraction steps, or more than two aqueous extraction steps, and the aqueous extracts obtained from the different extraction steps can be combined. One embodiment of the present invention provides a two-step extraction, which comprises extracting the mixture of Cyclocarya paliurus leaves, Puerariae lobatae Radix and Polygonati odorati Rhizoma with a first portion of water to obtain a first aqueous extract; extracting the mixture again with a second portion of water to obtain a second aqueous extract; and combining the first and second aqueous extracts to yield the aqueous extract ready for the later steps of the method. In particular, the water used in the extraction step(s) can be boiling water (at or above 100° C.), or hot water with a temperature higher than 37° C. and lower than 100° C. Alternatively, the extraction mixture can be boiled in water to provide the boiling water in any of the extraction steps.

The duration of the individual aqueous extraction steps can be optimized and determined by persons skilled in the art. For example, each aqueous extraction step can take about any of 1, 2, 3, 4, 5, 6, 7, 8, 9, 10, 11, or 12 hours. In a preferred embodiment of the two-step extraction in the method, the duration of the first extraction step is about 1-3 (such as about 2) hours, and the duration of the second extraction step is about 0.5-1.5 (such as about 1) hour. In another embodiment, the duration of the first extraction step is more than about 2 hours but less than about 12 hours, and the duration of the second extraction step is more than about 1 hour but less than about 6 hours.

The amount of water used in the extraction steps can be about any of 1 time, 2 times, 3 times, 4 times, 5 times, 6 times, 7 times, 8 times, 9 times, 10 times, 11 times, 12 times, 13 times, 14 times, 15 times, 16 times, 20 times, or more than 20 times by weight of the mixture of Cyclocarya paliurus leaves, Puerariae lobatae Radix and Polygonati odorati Rhizoma provided in step i) of the method. For example, in a preferred embodiment of the two-step extraction, the first portion of water is about 12 times by weight of the mixture of Cyclocarya paliurus leaves, Puerariae lobatae Radix and Polygonati odorati Rhizoma, and the second portion of water is about 10 times by weight of the mixture of Cyclocarya paliurus leaves, Puerariae lobatae Radix and Polygonati odorati Rhizoma. In another embodiment, the first portion of water is about 8-15 times by weight of the mixture of Cyclocarya paliurus leaves, Puerariae lobatae Radix and Polygonati odorati Rhizoma. In another embodiment of the present invention, the second portion of water is about 8-12 times by weight of the mixture of Cyclocarya paliurus leaves, Puerariae lobatae Radix and Polygonati odorati Rhizoma. A person skilled in the art can combine the amount of water in any of the embodiments described herein according to actual production situation.

In some embodiments, an optional filtration step can accompany each of the individual extraction steps, wherein the extract is filtered through a mesh filter (e.g. 150-50 mesh, or preferably an 80-mesh filter) to remove insoluble particles, which may contain toxic substances and/or heavy metals. For example, an 80-mesh filter has a pore size of about 177 μm, and a 150 mesh filter has a pore size of about 105 μm. Any particles larger than the pore size will be discarded after the optional filtration step(s), and the filtrate(s) will be combined for further steps in the method.

In some embodiments, prior to the concentration step iii), the aqueous extract is filtered through a mesh (e.g. 200-40 mesh, or preferably 100-mesh) filter to obtain a filtrate to be applied in the concentration step. For example, a 100-mesh filter has a pore size of about 149 μm, thereby effectively removes from the aqueous extract particles larger than about 149 μm, which can contain substances not useful for lowering blood sugar, or contain toxic substances causing undesirable side effects. In some embodiments of the filtration step, a 150-50 mesh filter (about 0.105-0.297 mm in pore size) can be used to remove large insoluble particles. The aqueous extract from individual extraction steps can be filtered prior to the filtrates being combined into one filtered aqueous extract, or the filtration step can be applied to the combined aqueous extract from individual extraction steps to obtain the filtered aqueous extract.

In one embodiment, chitosan is optionally added to the filtered aqueous extract (e.g. about 1% by weight of the herbal mixture), and mixed, for example, for about 15 minutes. The mixture with chitosan is allowed to stand overnight, and then filtered through a mesh (e.g. 200-40 mesh, or preferably 200 mesh) filter to obtain a filtrate with reduced heavy metal contents for the concentration step iii). Alternatively, in another embodiment, chitosan is optionally added to the filtered aqueous extract (e.g. about 1% by weight of the herbal mixture), and mixed for about 15 minutes, and centrifuged (e.g. at about 4000-8000 rpm, 5000-7000 rotations/min, or preferably at about 5380 rpm, for about 15 minutes) to obtain a supernatant with reduced heavy metal contents for the concentration step iii).

In one preferred embodiment, the concentration step iii) comprises concentrating the aqueous extract by heating the aqueous extract at about 50~90° C. (such as about 65~80° C.) under a vacuum of about −0.09~−0.02 (such as about −0.08~−0.04) MPa to obtain a concentrated mixture having a relative density of about 1.0-1.2 (such as about 1.1, as measured at about 60° C.). The vacuum pressure specified in this embodiment is measured with respect to the atmospheric pressure, which is about 0.10 MPa. Therefore, the absolute vacuum pressure in this embodiment is about 0.02-0.06 MPa. It should be pointed out that the temperature and vacuum pressure used in the concentration step can be adjusted by persons skilled in the art according to actual production situation. The relative density of the concentrated mixture is measured with respect to the density of water, which is about 1 g/mL. In another embodiment of the present invention, the relative density of the concentrated mixture can be about 1.0-1.2 when measured at about 60° C.

To further remove insoluble particles from the aqueous extract, step iv) of the method can comprise obtaining a liquid portion of the concentrated mixture by allowing the concentrated mixture to stand at about 0-6° C. (such as about 4° C.) for more than about 10 hours (such as about 12 hours) and taking a liquid portion that excludes the precipitate. In some embodiments, the concentrated mixture is allowed to stand for about any of 4 hours, 6, hours, 8 hours, 10 hours, 12 hours, 16 hours, 20 hour, or 24 hours. The precipitate or small solid particles discarded in this step may contain additional substances that are toxic, or ineffective in reducing blood sugar. In one embodiment, the concentrated mixture after standing is further filtered through a mesh (e.g. 200-40 mesh, or preferably 200-mesh) filter to remove the solid particles. In some embodiments, the concentrated mixture is centrifuged (e.g. at 5000-7000 rpm, or 5380 rpm) for about any of 10 minutes, 15 minutes, 20 minutes, 25 minutes, 30 minutes, or longer than 30 minutes, or preferably about 15 minutes to further reduce the heavy metal contents prior to the spray-drying step v) of the method.

The spray-drying step v) of the method in some embodiments of the present invention comprises spray-drying the liquid portion of the concentrated mixture in a spray-drying chamber having an in-flow temperature at about 170° C.-250° C. (such as about 180° C.-200° C.) and an out-flow temperature of about 60° C.-120° C. (such as about 80° C.-100° C.) to produce the herbal extract composition. The in-flow and out-flow temperatures of this step can be further adjusted according to actual situation.

Finally, the method for preparing the herbal extract composition can further comprise packing and sealing the herbal extract composition in a sterile package. The sterile package can be a plastic package, a paper package, a nylon package or any package deemed suitable by persons skilled in the art. The herbal extract composition can be placed in a single-layered sterile package, or a double-layered sterile package.

Accordingly, an herbal extract composition prepared by any embodiment of the method detailed herein is provided by the present invention. Any of the individual steps and parameters described herein can be combined to prepare the herbal extract composition comprising (including consisting essentially of or consisting of) an extract of *Cyclocarya paliurus* leaves, Puerariae lobatae Radix and Polygonati odorati Rhizoma. Example 1 describes such an exemplary method and the herbal extract composition prepared by this method.

Because of the multiple-step preparation method, the herbal extract composition provided by the present invention is characterized by a low concentration of heavy metals and other toxic elements. Common heavy metals found in Chinese medicine compositions include manganese, copper, cadmium, lead, iron, mercury, zinc and arsenic. In some embodiments, the herbal extract composition detailed herein contains a total of about less than 20 ppm (parts per million), less than 15 ppm, less than 10 ppm, less than 5 ppm, less than 1 ppm, or less than 0.5 ppm of combined heavy metal content. In some embodiments, the herbal extract composition contains about less than 5 ppm, less than 2 ppm, less than 1 ppm, less than 0.5 ppm, or less than 0.1 ppm of lead; and/or about less than 3 ppm, less than 2 ppm, less than 1 ppm, less than 0.5 ppm, or less than 0.1 ppm of arsenic; and/or about less than 3 ppm, less than 2 ppm, less than 1 ppm, less than 0.5 ppm, or less than 0.1 ppm of mercury. The low level of heavy metals ensures safety for long-term human consumption of the herbal extract composition and its derived compositions and products.

The heavy metal contents in the crude herbs (i.e. *Cyclocarya paliurus* leaves, Puerariae lobatae Radix and Polygonati odorati Rhizoma) that are used to prepare the herbal extract composition can vary significantly depending on their origins of production, thereby affecting the overall heavy metal contents of the herbal extract composition and its derivate products (e.g. pharmaceutical compositions, nutritional compositions, granules and other forms of products comprising the herbal extract composition). Table 1 lists representative concentrations of lead and arsenic as measured using methods known in the art in crude *Cyclocarya paliurus* leaves, Puerariae lobatae Radix and Polygonati odorati Rhizoma from various origins where the herbs are harvested and optionally processed prior to their use in producing the herbal extract composition. To warrant a desirable heavy metal content, in some embodiments of the method for preparing the herbal extract composition, *Cyclocarya paliurus* leaves, Puerariae lobatae Radix and Polygonati odorati Rhizoma from origins that are associated with low overall heavy metal contents, or low concentrations of particular heavy metals (such as lead and/or arsenic) as described herein are selected.

TABLE 1

Heavy metal contents in exemplary crude herbs from different origins

| Crude herbs | Origin | Lead (ppm) | Arsenic (ppm) |
|---|---|---|---|
| *Cyclocarya paliurus* leaves | Sui Ning, Hunan Province | 1.1 | 0.17 |
| | Shi En, Hubei Province | 1.4 | 0.15 |
| | Zhang Jia Jie, Hunan Province | 1.8 | 0.16 |
| | Huang Ao Xiang, Jiangxi Province | 1.7 | <0.5 |
| | Guan Shan, Jiangxi Province | 3.7 | 0.33 |
| | Da Lian Shan Jiangxi Province | 2.3 | 0.27 |
| *Puerariae lobatae Radix* | Anhui Province | 0.23 | 0.10 |
| *Polygonati odorati Rhizoma* | Hunan Province | 0.47 | 0.16 |

Besides the extract from the mixture of *Cyclocarya paliurus* leaves, Puerariae lobatae Radix and Polygonati odorati Rhizoma, the herbal extract composition can contain additional components, such as auxiliary components, to ensure desirable physiochemical and biopharmaceutical properties, for example stability and bioaccessibility of active substances. In some aspects, the herbal extract composition disclosed in the present invention can be incorporated in a nutritional composition, which may further comprise dietary materials and carriers. Examples of dietary materials and carriers include, but are not limited to, starch, talc, magnesium stearate, powdered milk, vitamins, flavoring agents, preservatives, dyes, and combinations thereof.

Likewise, the herbal extract composition can be incorporated in a pharmaceutical composition comprising any embodiment of the herbal extract composition detailed herein and a pharmaceutically acceptable carrier. "Pharmaceutically acceptable carrier" refers to a solid or liquid filler or gelatin material, which is compatible with the herbal extract composition, and is suitable to be used in human with sufficient purity and sufficiently low toxicity. Examples of pharmaceutically acceptable carrier include cellulose and its derivatives, gelatin, colorants, flavoring agents, stabilizers, and the like. In one embodiment of the present invention, the pharmaceutical composition comprises any of the herbal extract compositions detailed herein and mannitol.

In some embodiments, the ratio (by weight) of mannitol used in preparing of the pharmaceutical composition to the mixture of *Cyclocarya paliurus*, Puerariae lobatae Radix and Polygonati odorati Rhizoma used in preparing the herbal extract composition is about 1:4 to about 1:3, about 1:3 to about 1:2, about 1:3 to about 1:1, about 1:1 to about 2:1, about 2:1 to about 3:1, about 3:1 to about 4:1, about 7:20 to about 11:20, or preferably about 9:20. In some embodiments, the percentage by weight of mannitol in the pharmaceutical composition is 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, or preferably about 60%. In one embodiment, the pharmaceutical composition is prepared from an extract of a mixture of *Cyclocarya paliurus* leaves, Puerariae lobatae Radix and Polygonati odorati Rhizoma, and adding mannitol, wherein the relative proportion (by weight) of *Cyclocarya paliurus* leaves, Puerariae lobatae Radix, Polygonati odorati Rhizoma, and mannitol is about 35:35:30:45. In a preferred embodiment, the pharmaceutical composition comprises an extract from a mixture of about 3500 parts by weight (such as 3500 grams) of *Cyclocarya paliurus* leaves, about 3500 parts by weight (such as 3500 grams) of Puerariae lobatae Radix, and about 3000 parts by weight (such as 3000 grams) of Polygonati odorati Rhizoma, together with about 4500 parts by weight (such as 4500 grams) of mannitol as an auxiliary component. The relative proportion of *Cyclocarya paliurus*, Puerariae lobatae Radix and Polygonati odorati Rhizoma and the various auxiliary components in any of the compositions detailed herein can be reasonably adjusted by persons skilled in the art according to actual production situation.

The herbal extract composition, the nutritional composition, and the pharmaceutical composition detailed herein are useful for lowering blood sugar. The herbal extract composition can be used in the manufacture of a medicament for lowering blood sugar in a subject in need thereof.

Granules and Methods of Making Granules

The present invention provides a method for preparing a granule comprising an herbal extract composition and an excipient (such as mannitol). The method comprises the following steps:

1) mixing the herbal extract composition with an excipient (such as mannitol) to obtain a uniform mixture;

2) treating a portion of said mixture with an alcoholic solvent to obtain a wet granule; and 3) drying the wet granule to obtain a dry granule.

The present invention further provides a method for preparing a granule comprising an herbal extract composition comprising (including consisting essentially of or consisting of) an extract of *Cyclocarya paliurus*, Puerariae lobatae Radix and Polygonati odorati Rhizoma, as well as an excipient (such as mannitol). The method comprises steps 1)-3) of the preceding method, wherein the herbal extract composition is prepared by the method comprising:

i) providing a mixture of *Cyclocarya paliurus* leaves, Puerariae lobatae Radix and Polygonati Odorati Rhizoma;

ii) extracting said mixture with water (such as boiling water) to obtain an aqueous extract;

iii) concentrating the aqueous extract to obtain a concentrated mixture;

iv) obtaining a liquid portion of said concentrated mixture; and v) drying (e.g., spray-drying) said liquid portion to produce an herbal extract composition.

The relative proportion (by weight) of each ingredient provided to make the granule can be important for optimum function of the granule. In some embodiments, a predetermined amount of the herbal extract composition and a predetermined amount of the excipient (such as mannitol) are first weighed to be used in the method for making the granule. The excipient (such as mannitol) can be first crushed. The crushed excipient (such as mannitol) can further be sieved through a mesh sieve, such as a 120-mesh to 50-mesh, for example an 80-mesh (pore size 0.177 mm) sieve, to remove large particles. In some embodiments, the ratio (by weight) of the excipient (such as mannitol) to the mixture of *Cyclocarya paliurus*, Puerariae lobatae Radix and Polygonati odorati Rhizoma used to prepare the granule is about 1:4 to about 1:3, about 1:3 to about 1:2, about 1:3 to about 1:1, about 1:1 to about 2:1, about 2:1 to about 3:1, about 3:1 to about 4:1, or preferably about 9:20. In some embodiments, the percentage by weight of the excipient (such as mannitol) in the granule is 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, or preferably about 60%. The relative proportion of *Cyclocarya paliurus*, Puerariae lobatae Radix and Polygonati odorati Rhizoma and the various auxiliary components in the granule detailed herein can be reasonably adjusted by persons skilled in the art according to actual production situation. In an exemplary embodiment, the granule is prepared from the herbal extract composition, which is prepared from an extract of a mixture of about 35 times weight (e.g. about 3500 grams) of *Cyclocarya paliurus* leaves, about 35 times weight (e.g. about 3500 grams) of Puerariae lobatae Radix, and about 30 times weight (e.g. about 3000 grams) of Polygonati odorati Rhizoma, as well as about 45 times weight (e.g. about 4500 grams) of the excipient (such as mannitol). The relative amounts of the components, such as the herbal extract composition, and the excipient (such as mannitol) can be in any of the ratios described herein.

Several other parameters of the method for preparing the granule can be important. Also, additional steps and modifications to the steps in the method can be helpful for optimization of the granule. In one preferred embodiment, the first mixing step 1) of the method comprises mixing the herbal extract composition with the excipient (such as mannitol) for about 2-10 minutes to obtain a uniform mixture. The duration of this mixing step can be longer than 10 minutes (such as 20 minutes) to ensure desirable uniformity.

In step 2) of the method, the alcoholic solvent used to treat the mixture can be 95% ethanol in aqueous solution, or another alcohol or alcoholic solution of comparable extraction capacity and properties that is commonly used in food production. In order to screen for granules of appropriate size, step 2) of the method can further comprise a step of sieving the wet granules through a sieve, such as a 20-mesh to 10-mesh sieve, prior to drying the granules. For example, a 20-mesh sieve has a pore size of about 0.841 mm, thereby allowing wet granules with a particle size smaller than about 0.841 mm to be selected for further processing into the dry granules. A sieve of comparable pore size, such as a 10-mesh (about 1.68 mm pore size) to 25-mesh (about 0.707 mm pore size) to sieve can be applied in this sieving step in some embodiments of the present invention.

One preferred set of conditions for drying the wet granule in step 3) of the method requires a temperature of about 40° C.-90° C. (such as about 65° C.-75° C.) for drying, and the dry granule contains less than about 5% water. In some embodiments, the dry granule contains about less than 4% water, less than 2% water, or less than 1% water. A sieving step for the dry granule can also be included in step 3), in which the dry granule is sieved through two sieves with different pore sizes to select for granules with a particle size between the pore sizes of the two sieves. In one embodiment, the dry granule is sieved through a 10-mesh sieve (pore size 1.68 mm) and a 100-mesh (pore size 0.149 mm), yielding a dry granule larger than 0.149 mm and smaller than 1.68 mm. In one embodiment, the dry granule is sieved through a 20-mesh sieve (pore size 0.841 mm) and an 80-mesh (pore size 0.177 mm), yielding a dry granule larger than 0.177 mm and smaller than 0.841 mm. Sieves with comparable pore sizes can be used in other embodiments that select for dry granules of other particle sizes.

In some embodiments, the method further comprises a mixing step after drying and optional sieving, wherein the dry granule is mixed for about 10-30 (such as about 10) minutes to obtain a uniform mixture. The duration of the additional mixing step can be longer than 30 minutes to obtain a mixture of desirable uniformity. Additional steps comprising packaging and testing for quality control can be included in the method for preparing the granule according to production standards.

It is intended that any of the steps and parameters described herein for preparing the herbal extract composition comprising (including consisting essentially of or consisting of) *Cyclocarya paliurus*, Puerariae lobatae Radix and Polygonati odorati Rhizoma can be combined with any of the steps and parameters described herein for preparing the granule, as if each and every combination is individually described. For example, in one embodiment, a granule comprising an herbal extract composition comprising (including consisting essentially of or consisting of) *Cyclocarya paliurus*, Puerariae lobatae Radix and Polygonati odorati Rhizoma, which further comprises mannitol, is prepared by the method comprising weighing out a starting mixture of about 35 times weight (e.g. about 3500 grams) of *Cyclocarya paliurus* leaves, about 35 times weight (e.g. about 3500 grams) of Puerariae lobatae Radix, and about 30 times weight (e.g. about 3000 grams) of Polygonati odorati Rhizoma; extracting said starting mixture with a first portion of about 8-15 (such as about 12) times (by weight of said starting mixture) of water (e.g., boiling water) for about 1-3 (such as about 2) hours to obtain a first aqueous extract; further extracting said starting mixture with a second portion of about 8-12 (such as about 10) times (by weight of said starting mixture) for about 0.5-1.5 (such as about 1) hour to obtain a second aqueous extract; filtering said first aqueous extract through a 150-mesh to about 50-mesh (such as about 100-mesh) filter to obtain a first filtrate; filter said second aqueous extract through a 150-mesh to about 50-mesh (such as about 100-mesh) filter to obtain a second filtrate; combining said first filtrate and said second filtrate to give a combined filtrate; concentrating the combined filtrate by heating the combined filtrate at about 50~90° C. (such as about 65~80° C.) under a vacuum of about −0.09~−0.02 (such as −0.08~−0.04) MPa to obtain a concentrated mixture, wherein the concentrated mixture has a relative density of about 1.0-1.2 (such as about 1.1, as measured at about 60° C.); allowing the concentrated mixture to stand at about 0-6° C. (such as about 4° C.) for more than about 10 hours (such as about 12 hours) and taking a liquid portion of the concentrated mixture; spray-drying said liquid portion in a spray-drying chamber having an in-flow temperature at about 170° C.~250° C. (such as about 180° C.~200° C.) and an out-flow temperature of about 60° C.~120° C. (such as about 80° C.~100° C.) to produce an herbal extract composition; weighing out about 45 times weight (e.g. about 4500 grams of) mannitol; crushing the mannitol; sieving the crushed mannitol through a 120-mesh to 50-mesh (such as about 80-mesh) sieve; mixing said sieved mannitol with the herbal extract composition for about 2-10 minutes to obtain a uniform mixture; treating the first uniform mixture with 95% ethanol used for food production to obtain a wet granule; sieving the wet granule through a 20-mesh to 10-mesh (such as 20-mesh) sieve to obtain a wet granule with particle size smaller than 20-mesh to 10-mesh; drying the wet granule with particle size smaller than 20-mesh to 10-mesh at about 40° C.~90° C. (such as about 67° C.~75° C.) to obtain a dry granule, wherein the dry granule contains less than about 5% water; sieving the dry granule through a 10-mesh sieve and an 100-mesh sieve to obtain a straightened dry granule with particle size smaller than 10-mesh and larger than 100-mesh; mixing the dry granule for about 10-30 (such as about 10) minutes to obtain a uniform dry granule; packing about 0.03 times weight (e.g. about 3 grams) of the uniform dry granule into a package; placing the packed dry granule into an outer package and testing the packaged granule for quality control.

In another embodiment, a granule comprising an herbal extract composition comprising (including consisting essentially of or consisting of) *Cyclocarya paliurus* leaves, Puerariae lobatae Radix and Polygonati odorati Rhizoma, which further comprises mannitol, is prepared by the method comprising weighing out a starting mixture of about 35 times weight (e.g. about 3500 grams) of *Cyclocarya paliurus* leaves, about 35 times weight (e.g. about 3500 grams) of Puerariae lobatae Radix, and about 30 times weight (e.g. about 3000 grams) of Polygonati odorati Rhizoma; optionally washing said starting mixture with water for 3 times; extracting said starting mixture with a first portion of about 8-15 (such as about 12) times (by weight of said starting mixture) of water (such as boiling water) for about 1-3 (such as about 2) hours to obtain a first aqueous extract; optionally filtering the first aqueous extract through a mesh filter (e.g. 200-40 mesh, or preferably 80-mesh) to obtain a first filtered aqueous extract; further extracting said starting mixture with a second portion of about 8-12 (such as about 10) times (by weight of said starting mixture) of water (such as boiling water) for about 0.5-1.5 (such as about 1) hour to obtain a second aqueous extract; optionally filtering the second aqueous extract through a mesh filter (e.g. 200-40 mesh, or preferably 80-mesh) to obtain a second filtered aqueous extract; combining said first (filtered) aqueous extract and said second (filtered) aqueous extract to give a combined aqueous extract; optionally filtering said combined aqueous extract through a mesh (e.g. 200-40 mesh, or preferably 200-mesh) filter; concentrating the combined (filtered) aqueous extract (e.g. to about 400 mL) to obtain a concentrated mixture; allowing the concentrated mixture to stand at about 0-6° C. (such as about 4° C.) for more than about 10 hours (such as about 12 hours) and taking a first liquid portion of the concentrated mixture; optionally centrifuging said first liquid portion for about 15 minutes at about 4000-8000 rpm (e.g. 5380 rpm) and taking a second liquid portion of the centrifuged concentrated mixture to obtain the herbal extract composition; weighing out about 45 times weight (e.g. about 4500 grams of) mannitol; crushing the mannitol; sieving the crushed mannitol through a 120-mesh to 50-mesh (such as about 80-mesh) sieve; mixing said sieved mannitol with the herbal extract composition for about 2-10 minutes to obtain a uniform mixture; treating the first uniform mixture with 95% ethanol used for food production to obtain a wet granule; sieving the wet granule through a 20-mesh to 10-mesh (such as 20-mesh) sieve to obtain a wet granule with particle size smaller than 20-mesh to 10-mesh; drying the wet granule with particle size smaller than 20-mesh to 10-mesh at about 40° C.~90° C. (such as about 67° C.~75° C.) to obtain a dry granule, wherein the dry granule contains less than about 5% water; sieving the dry granule through a 10-mesh sieve and an 100-mesh sieve to obtain a straightened dry granule with particle size smaller than 10-mesh and larger than 100-mesh; mixing the dry granule for about 10-30 (such as about 10) minutes to obtain a uniform dry granule; packing about 0.03 times weight (e.g. about 3 grams) of the uniform dry granule into a package; placing the packed dry granule into an outer package and testing the packaged granule for quality control.

Methods for Use

One aspect of the present invention provides a method of lowering blood sugar in a subject in need thereof comprising administering to the subject a therapeutically effective amount of an herbal extract composition, a granule, a nutritional composition, or a pharmaceutical composition described herein, each independently, comprising (including consisting essentially of or consisting of) an extract of *Cyclocarya paliurus* leaves, Puerariae lobatae Radix and Polygonati odorati Rhizoma. The subject in need can be a human patient suffering from diabetes, other metabolic diseases, or other conditions associated with an elevated blood sugar level. Blood sugar refers to the variety of naturally occurring carbohydrates, including monosaccharides, oligosaccharides, and polysaccharides that are normally found in the blood stream, blood or any serological fraction of the blood, such as serum. One monosaccharide species, glucose, is the primary source of energy for cells in all organisms, and therefore, glucose is one of the most abundant and highly regulated sugars in the blood. In some but not all embodiments of the present invention, "lowering blood sugar" specifically refers to lowering blood glucose. Lowering of blood sugar is an effective strategy to treat and manage human conditions, such as diabetes and other metabolic conditions that are responsive to reduced blood sugar level. Therefore, the method described herein can also be applied to treat any disease or condition responsive to lowering of blood sugar.

Alternatively, the herbal extract composition, the granule or the nutritional composition described herein can be used as a nutritional supplement in a method provided by the present invention to reduce blood sugar in a subject in need thereof. "Nutritional supplement" refers to substance that may have beneficial health effects, but are normally absent or present at insufficient quantities in a person's diet. As a nutritional supplement, the herbal extract composition, the granule, or the nutritional composition should be administered to the subject in need thereof in conjunction with standard and other therapeutic means to help the subject manage his or her blood sugar levels.

"Therapeutically effective amount" or "effective amount" in the present invention refers to an amount of the herbal extract composition, the granule, the nutritional composition, or the pharmaceutical composition sufficient to improve the condition of the subject in need thereof, without causing serious side-effects. In a preferred embodiment of the present invention, the granule described in Examples 1 and 2 are administered orally with a dosage regimen of 2 doses per day and 1 packet of granule (about 3 g portion) per dose. A recommended method to administer the granule is to place one packet of the granule in a glass, add about 4-6 oz. of cold or warm water, mix thoroughly, and take the infusion. The dosage of the herbal extract composition, the granule, the nutritional composition, or the pharmaceutical composition of the present invention can be adjusted according to actual situation based on knowledge known in the art. The efficacy of the herbal extract composition, the granule, the nutritional composition, or the pharmaceutical composition can be measured by methods known in the art for assessing blood sugar levels in standard animal models (e.g. mice and rats) or in human subjects, for example, as illustrated in Example 8.

EXAMPLES

The following exemplary embodiments further describe the present invention. Although the description refers to practical embodiments, it will be clear to one skilled in the art that the present invention may be practiced with variation of these specific details. Hence this invention should not be construed as limited to the embodiments set forth herein.

Example 1 Preparation of an Herbal Extract Composition

A flow chart illustrating an exemplary method for preparing an herbal extract composition comprising (including consisting essentially of or consisting of) an extract of *Cyclocarya paliurus* leaves, Puerariae lobatae Radix and Polygonati odorati Rhizoma is shown in FIG. 2, and described below.

The following steps were performed to prepare the herbal extract composition. The quality of *Cyclocarya paliurus* leaves, Puerariae lobatae Radix and Polygonati odorati Rhizoma were inspected according to ingredient standards. Then, about 3500 grams of *Cyclocarya paliurus* leaves, about 3500 grams of Puerariae lobatae Radix and about 3000 grams of Polygonati odorati Rhizoma were weighed out according to the recipe shown in Table 2. The weighed *Cyclocarya paliurus* leaves, Puerariae lobatae Radix and Polygonati odorati Rhizoma (starting material mixture) were placed into a multi-function extractor. The mixture was extracted two times with water. About 8-15 (such as 12) times water by weight of the starting material mixture was added for the first extraction, and the mixture was boiled for about 1-3 (such as about 2) hours to obtain a first aqueous extract. About 8-12 (such as about 10) times water by weight of the starting material mixture was then added, and the mixture was boiled for about 0.5-1.5 (such as about 1) hour to obtain a second aqueous extract. The first and the second aqueous extracts were filtered through a 150-mesh to 100-mesh (such as 100-mesh) filter to obtain filtrates, the filtrates were combined, and the remnants were discarded. The combined filtrate was concentrated in a vacuum concentrator, in which the temperature was maintained at about 50-90° C., and the vacuum pressure was maintained at about −0.09~−0.02 MPa, until the concentrated liquid achieved a relative density of about 1.0-1.2 (such as about 1.1, measured at about 60° C.) to obtain a concentrated liquid. The concentrated liquid was placed in cold storage, and allowed to stand for more than about 10 hours (such as about 12 hours) at about 0-6° C. (such as about 4° C.). A portion of the supernatant from the concentrated liquid was taken after standing, and the precipitate was discarded. The chamber of a spray dryer was preheated until achieving an in-flow temperature of about 170° C.~250° C. and an out-flow temperature of about 60° C.~120° C. Then, the supernatant was placed in the spray dryer. The flow rate and air speed were adjusted after the supernatant was inside the spray dryer, so that the out-flow temperature was maintained at about 60° C.~120° C. An herbal extract composition was obtained after drying. The herbal extract composition was sealed in a double-layered sterile plastic bag. The method parameters described herein can be adjusted according to actual situation.

Example 2 Preparation of Granules

Figure 3:
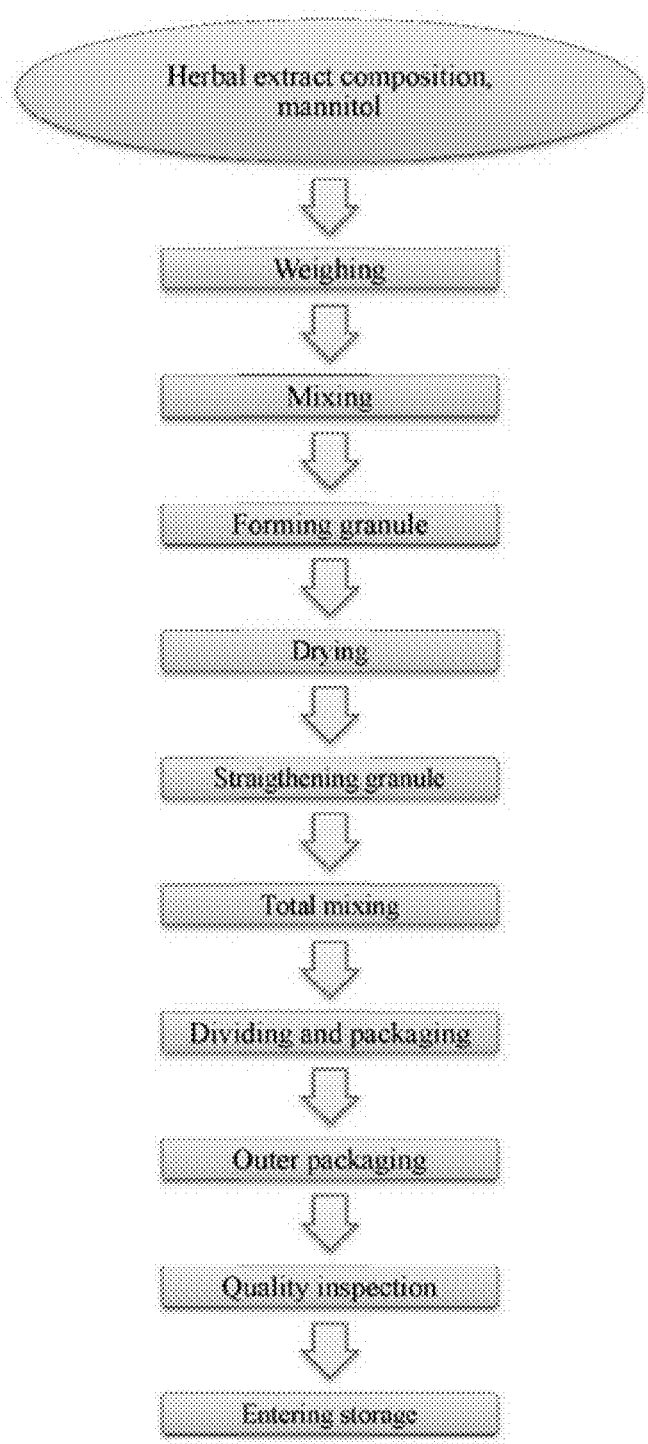
FIG. 3 shows a schematic flow chart of an exemplary embodiment of a method for preparing a granule comprising an herbal extract composition and mannitol.
Figure 4:
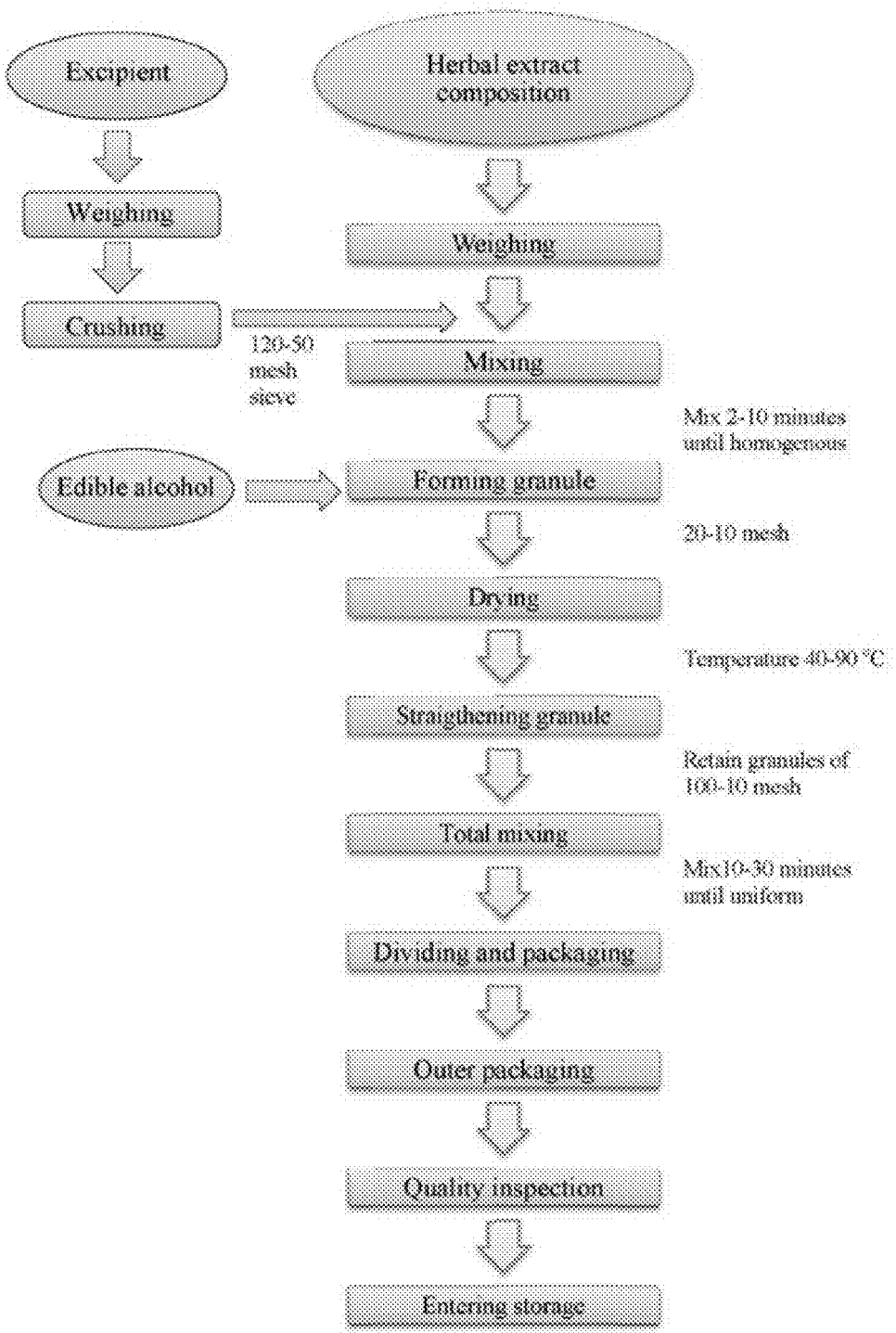
FIG. 4 shows a schematic flow chart of an exemplary embodiment of a method for preparing a granule comprising an herbal extract composition and an excipient (e.g., mannitol).

A flow chart illustrating an exemplary method for preparing a granule comprising an herbal extract composition comprising (including consisting essentially of or consisting of) an extract of *Cyclocarya paliurus* leaves, Puerariae lobatae Radix and Polygonati odorati Rhizoma is shown in FIG. 3, and described below.

The following steps were performed to prepare the granule. Mannitol was sieved through a 120-mesh to 50-mesh sieve (such as 80-mesh) sieve. Then the herbal extract composition prepared by the method in Example 1 was provided, and about 4500 grams of sieved mannitol was weighed out according to the recipe in Table 2. The herbal extract composition and mannitol were mixed for about 2-10 minutes to obtain a uniform mixture. The mixture was treated with 95% ethanol in food production to obtain a wet granule. The wet granule was sieved through a 20-mesh to about 10-mesh (such as about 20-mesh) sieve to remove large particles. The sieved wet granule was dried in a drying oven at a temperature of about 40° C.~90° C. (such as 65° C.~70° C.) to obtain a dry granule containing less than about 5% water. The dry granule was sieved through a 10-mesh sieve and a 100-mesh sieve to select for a straightened dry granule with a particle size smaller than 10-mesh and larger than 100-mesh. The straightened dry granule was mixed for about 10-30 minutes to obtain a uniform granule. A portion of about 3 grams of the uniform granule was packed into a package. The variation in the weight of granules packed per package was controlled within ±5%. The quality of packaging was inspected. The granule package was placed into an outer package, and the quality of the packaged granule was inspected according to company standards. The packaged granule that have passed quality inspections was entered into storage, and stored in a cool and dry warehouse. The method parameters described herein can be adjusted according to actual situation. For preparation of 1000 packets of granules, 3 g/packet, the yield of the herbal extract composition is about 30%. The weight of ingredients can be adjusted according to actual production situation.

TABLE 2

| Recipe for preparing a granules | |
|---|---|
| Ingredients | Weight |
| *Cyclocarya paliurus* leaves | 3500 g |
| Puerariae lobatae Radix | 3500 g |
| Polygonati odorati Rhizoma | 3000 g |
| mannitol | 4500 g |

The granules are administered, for example, to a human at one packet at a time, 2 times per day.

Example 3 Preparation of Granules

A flow chart illustrating an exemplary method for preparing a granule comprising an herbal extract composition and an excipient (e.g., mannitol) is shown in FIG. 3.

The excipient (e.g. mannitol) is crushed and sieved through a 120-mesh to 50-mesh sieve, and then mixed with the herbal extract composition in about 2~10 minutes until uniform. The mixture is treated with edible alcohol to form wet granules. The wet granules are sieved through a 20-mesh to 10-mesh sieve and dried at 40° C.~90° C. The dried granules are straightened and granules having a size of about 100-mesh to 10-mesh are retained for packaging. The dry granules are divided into desirable portions and packed in an inner packaging, then wrapped in an outer packaging. The product is tested for quality control and placed in storage.

Example 4 Preparation of Test Samples and Control Samples

Sample Formulae:

Test Sample 1 (S1): *Cyclocarya paliurus* leaves 1.0 kg, Puerariae lobatae Radix 8.0 kg, and Polygonati odorati Rhizoma 1.0 kg.

Test Sample 2 (S2): *Cyclocarya paliurus* leaves 2.0 kg, Puerariae lobatae Radix 1.0 kg, and Polygonati odorati Rhizoma 7.0 kg.

Test Sample 3 (S3): *Cyclocarya paliurus* leaves 3.5 kg, Puerariae lobatae Radix 3.5 kg, and Polygonati odorati Rhizoma 3.0 kg.

Test Sample 4 (S4): *Cyclocarya paliurus* leaves 6.0 kg, Puerariae lobatae Radix 2.0 kg, and Polygonati odorati Rhizoma 2.0 kg.

Test Sample 5 (S5): *Cyclocarya paliurus* leaves 8.0 kg, Puerariae lobatae Radix 1.0 kg, and Polygonati odorati Rhizoma 1.0 kg.

Test Sample 6 (S6): *Cyclocarya paliurus* leaves 1.0 kg, Polygonati odorati Rhizoma 1.0 kg, *Dioscoreae* Rhizoma 1.0 kg, Lycii Fructus 1.0 kg, Rhodiolae Crenulatae Radix et Rhizoma 1.0 kg, Ophiopogonis Radix 1.0 kg, Prepared Rhubarb 1.0 kg, *Schisandrae chinensis* Fructus 1.0 kg, Konjac 1.0 kg, and *Hericium erinaceus* 1.0 kg.

Control Sample 1 (D1): *Cyclocarya paliurus* leaves: 10 kg.

Control Sample 2 (D2): Puerariae lobatae Radix: 10 kg.

Control Sample 3 (D3): Polygonati odorati Rhizoma: 10 kg.

The samples were prepared according to the steps detailed below, and tested for efficacies in lowering blood sugars, blood lipids, and blood pressure in animal models.

Method of Preparation

Step 1. Each herbal medicine was weighed precisely according to the formula above, washed with clean water; extracted twice by boiling with 12 times (by weight) of water for 2 hours, and with 10 times (by weight) of water for 1 hour; and 100-mesh filtered.

Step 2. The extracts were combined and filtered; the filtrate was concentrated to a relative density of 1.05-1.08 when measured at 60° C.; and saved for later use.

Step 3. The filtrate was placed in a spray drier. The chamber was pre-heated, and the filtrate was allowed to enter when the inlet air temperature reached 210° C.~10° C. The flow rate and air speed were adjusted, and the outlet air temperature was controlled at 95° C.±5° C. to obtain an extract powder, which was sealed in a double-layered clean plastic bag.

Step 4. The extract powder was mixed with mannitol for about 3-5 mins.

Step 5. The mixture was made into soft material by soaking with 70% edible alcohol, filtered with 20 mesh to obtain wet granules; then the wet granules were dried to obtain dry granules.

Step 6. The dry granules were straightened using 20 mesh and 60 mesh filter, dry granules of less than 20 mesh and bigger than 60 mesh were aliquoted into bags, 3 g/bag.

The granule compositions can be made into multiple pharmaceutical dosage forms, such as capsules, granules, powder, tablets, effervescent tablets, oral solution, and tea bags, etc., using regular preparation methods known in the field.

Example 5 Test of Lowering Blood Sugar

1. Materials and Methods

1) Samples and solution: samples from Test Samples 1-6 and Control Samples 1-3 were labeled as S1, S2, S3, S4, S5, S6, and D1, D2, D3, respectively; Streptozotocin (SIGMA), pack size: 1 g/tube, lot#: SLBJ7785V; insulin detection kit, imported and aliquoted, Nanjing Jiancheng Bioengineering Co., 20141022; 0.9% NaCl injection (physiological saline), pack size: 250 mL/bottle, Sichuan Kelun Pharmaceutical Co. Ltd., lot#: C13102005-1; high fat diet formula (79% basal diet+1% cholesterol+15% fresh yolk+5% lard), picric acid, etc.

2) Instruments: W-80A vortex mixer (Shanghai Medical Instruments Co. Ltd.); electronic balance, METTLER TOLEDO (METTLER-TOLEDO group), model: pl303; LDZ5-2 centrifuge (Beijing Medical Centrifuge Factory); Johnson Stable Blood Glucose Meter (Johnson & Johnson (China) Medical Device Co. Ltd.); BECKMAN Synchron CX 5 automatic blood biochemistry analyzer (USA); microplate reader, Bio-Rad (USA), model: iMark; DCA 2000 glycosylated hemoglobin analyzer (Bayer, Germany); others: platform scale, and fixed cage, etc.

3) Experimental animals: SD rats (SPF level), weight 160-180 g, male, provided by Southern Medical University Laboratory Animal Center, Certificate#: SCXK (Guangdong) 2011-0015. Animals were raised in SPF level barrier level animal room, animal use license#: SYXK (Guangdong) 2012-0081.

4) Dosage setting: expected dosage for human adults is 3.0 g/60 kg·BW·day. Dosage used for rats was 10 times that of human. The dosage was calculated using raw drug amount.

5) Statistical analysis: data were processed using SPSS 17.0 statistical tool, parameters were displayed as mean±standard deviation (0.0±S), ANOVA test was used for comparison among groups, $p<0.05$ was defined as statistically significant.

2. Methods and Results 2.1 Methods

1) Rat diet: Regular diet: cornmeal 80%, flour 15%, soybean flour 5%; High fat diet: 79% basal diet+1% cholesterol+15% fresh yolk+5% lard.

2) Modeling: 110 SPF level SD rats, male, weight 160-180 g, were fed for one week adaptively. 10 rats were selected as normal control group and fed with regular diet, while animals of other groups were fed with high fat diet for one month, after random inspection showing an obvious elevation in blood lipid indexes, STZ was intraperitoneally injected at 35 mg/kg to induce diabetic models (before injecting, STZ was prepared into 6 mg/mL solution using 0.1 mmol/L citric acid/sodium citrate buffer (pH=4.5), and destined to be finished within 60 mins). Fasting venous blood was collected from tails on the $7^{th}$ day after STZ injection. Blood sugar was measured using blood sugar meter, and successful models were regarded as with blood sugar ≥16.7 mmol/L. After the models are stable, animals were grouped based on blood lipids and blood sugar, orally administered test drugs and control drugs, and all indexes were monitored.

3) Grouping and drug administration: 100 successfully modeled animals in relatively good conditions were evenly separated into 10 groups based on blood sugar levels and weights: 10 rats per group, named as type II diabetic model control group (administered with distilled water), S1 group, S2 group, S3 group, S4 group, S5 group, S6 group, D1 group, D2 group, and D3 group. Normal un-modeled SD rats were set as normal control (administered with distilled water). Each group was orally administered with drug according to corresponding dosage, once per day, for a period of 4 weeks (4 W).

2.2 Measurements

1) Regular observation was performed, and weights were recorded every 2 weeks.

2) Blood sugar was measured before, after 2 weeks and after 4 weeks of drug administration, using blood sugar meter.

3) Serum insulin and glycosylated hemoglobin levels were measured.

4) Sugar tolerance test: the test was carried out 2 days before the whole experiment ended. Sugar tolerance test was carried out as following: animals were kept under fasting for about 6 hours, different concentrations of test samples were given to each group, glucose was orally administered at 2.0 g/kg after 15-20 mins, blood sugar levels were measured at 0, 0.5, and 2 hours after administering glucose, and the changes of areas under the blood sugar curve of each time point after administering glucose were studied for both model control group and experimental groups. The area under the blood sugar curve=½×(blood sugar level at 0 h+blood sugar level at 0.5 h)×0.5+½×(blood sugar level at 2 h+blood sugar level at 0.5 h)×1.5=0.25×(blood sugar level at 0 h+4× blood sugar level at 0.5 h+3× blood sugar level at 2 h).

2.3 Results

1) The effect on blood sugar of type II diabetes rat: As shown in Table 3, the rat blood sugar levels of each diabetes model group significantly elevated before giving drugs, compared to that of the normal control group, indicating the diabetes model was successful. After 2 W drug administration, the blood sugar levels of S1-S6 groups and D1 group all decreased, compared to that of model control group. After 4 W of drug administration, the blood sugar levels of S1-S6 groups and D1 group all decreased.

TABLE 3

The effect of samples on blood sugar levels of type II diabetes rats ($\bar{x} \pm S$)

| Group | n | Blood sugar level before treatment (mmol/L) | Blood sugar level after 2 W treatment (mmol/L) | Blood sugar level after 4 W treatment (mmol/L) |
|---|---|---|---|---|
| Normal control group | 10 | 5.26 ± 1.02 | 5.41 ± 0.90 | 5.47 ± 1.05 |
| Model control group | 10 | 20.68 ± 3.45## | 21.03 ± 3.52## | 22.93 ± 3.45## |
| S1 group | 10 | 20.93 ± 3.30 | 17.86 ± 3.12* | 16.36 ± 3.51* |
| S2 group | 10 | 19.48 ± 3.15 | 17.53 ± 3.10* | 16.23 ± 3.12* |
| S3 group | 10 | 21.03 ± 3.11 | 17.21 ± 3.48* | 15.97 ± 2.73** |
| S4 group | 10 | 20.65 ± 3.40 | 17.72 ± 3.45* | 16.75 ± 3.29* |
| S5 group | 10 | 21.08 ± 2.86 | 17.65 ± 3.20* | 16.22 ± 3.16* |
| S6 group | 10 | 21.03 ± 2.93 | 17.45 ± 3.62* | 16.38 ± 3.53* |
| D1 group | 10 | 20.71 ± 2.95 | 17.90 ± 3.15* | 16.75 ± 3.49* |
| D2 group | 10 | 20.19 ± 3.30 | 19.86 ± 4.62 | 19.85 ± 4.80 |
| D3 group | 10 | 21.06 ± 3.17 | 19.95 ± 4.91 | 19.93 ± 4.02 |

Note:
compared to normal control group: #p < 0.05, ##p < 0.01;
compared to model control group: *p < 0.05, **p < 0.01.

The effects on serum insulin level and glycosylated hemoglobin level of type II diabetes rats: As shown in Table 4, compared to those of the normal control group, rats in model control group showed significantly decreased serum insulin level (p<0.01) and significantly elevated glycosylated hemoglobin level (p<0.01) after fed with high fat diet and modeled for diabetes, indicating hyperlipidemia rat models were successful. Compared to the model control group, rat serum insulin levels of S1-S6 groups and D1 group all increased. Compared to the model control group, rat glycosylated hemoglobin levels of S1-S6 groups and D1 group all decreased (p<0.05).

TABLE 4

The effect of samples on serum insulin level and glycosylated hemoglobin level of type II diabetes rats ($\bar{x} \pm S$)

| Group | n | Insulin (mmol/L) | Glycosylated hemoglobin (mmol/L) |
|---|---|---|---|
| Normal control group | 10 | 18.42 ± 2.83 | 3.65 ± 0.71 |
| Model control group | 10 | 8.92 ± 2.42## | 9.52 ± 1.41## |
| S1 group | 10 | 12.21 ± 2.35* | 6.96 ± 1.74* |
| S2 group | 10 | 12.52 ± 2.44* | 6.87 ± 1.62* |
| S3 group | 10 | 13.41 ± 1.83** | 6.42 ± 1.28** |
| S4 group | 10 | 12.40 ± 2.26* | 7.01 ± 1.36* |
| S5 group | 10 | 12.58 ± 2.19* | 7.10 ± 1.45* |
| S6 group | 10 | 12.69 ± 2.17* | 6.99 ± 1.29* |
| D1 group | 10 | 12.15 ± 2.11* | 6.95 ± 1.35* |
| D2 group | 10 | 9.87 ± 2.74 | 8.63 ± 2.31 |
| D3 group | 10 | 9.90 ± 2.85 | 8.54 ± 2.06 |

Note:
compared to normal control group: #p < 0.05, ##p < 0.01;
compared to model control group: *p < 0.05, **p < 0.01.

3) The sugar tolerance test results of type II diabetes rats: As shown in Table 5, the areas under the blood sugar curves of S1-S6 groups and D1 group all decreased, compared to that of model control group.

TABLE 5

The effect of samples on sugar tolerance of type II diabetes rats ($\bar{x} \pm S$)

| Group | n | Area under blood sugar curve |
|---|---|---|
| Normal control group | 10 | 12.14 ± 0.95 |
| Model control group | 10 | 38.60 ± 6.45## |
| S1 group | 10 | 30.22 ± 6.15* |
| S2 group | 10 | 31.57 ± 6.48* |
| S3 group | 10 | 27.94 ± 5.78** |
| S4 group | 10 | 28.89 ± 6.76* |
| S5 group | 10 | 30.81 ± 6.19* |
| S6 group | 10 | 31.30 ± 5.74* |
| D1 group | 10 | 30.44 ± 6.86* |
| D2 group | 10 | 35.47 ± 5.97 |
| D3 group | 10 | 36.83 ± 6.40 |

Note:
compared to normal control group: #p <0.05, ##p < 0.01;
compared to model control group: p > 0.05 for all.

3. Conclusion

S1-S6 and D showed clear effects on lowering blood sugar for diabetes model rats, and the compositions of S1-S6 exhibited synergistic or enhanced effects in lowering blood sugar.

Example 6 Test of Lowering Blood Lipids

Materials and Methods

1) Samples and solution: samples from Test Samples 1-6 and Control Samples 1-3 were labeled as S1, S2, S3, S4, S5, S6, and D1, D2, D3, respectively; 0.9% NaCl injection (physiological saline), pack size: 250 mL/bottle, Sichuan Kelun Pharmaceutical Co. Ltd., lot#: C13102005-1; high fat diet formula (79% basal diet+1% cholesterol+15% fresh yolk+5% lard), distilled water, and picric acid, etc.

2) Instruments: W-80A vortex mixer (Shanghai Medical Instruments Co. Ltd.); electronic balance, METTLER TOLEDO (METTLER-TOLEDO group), model: pl303; LDZ5-2 centrifuge (Beijing Medical Centrifuge Factory); BECKMAN Synchron CX 5 automatic blood biochemistry analyzer (USA); others: platform scale, and fixed cage, etc.

3) Experimental animals: SD rats (SPF level), weight 160-180 g, male, provided by Southern Medical University Laboratory Animal Center, Certificate#: SCXK (Guangdong) 2011-0015. Animals were raised in SPF level barrier level animal room, animal use license#: SYXK (Guangdong) 2012-0081.

4) Dosage setting: expected dosage for human adults is 3.0 g/60 kg·BW·day. Dosage used for rats was 10 times that of human. The dosage was calculated using raw drug amount.

5) Statistical analysis: data were processed using SPSS 17.0 statistical tool, parameters were displayed as mean±standard deviation (0.0±S), ANOVA test was used for comparison among groups, $p<0.05$ was defined as statistically significant.

Methods and Results 2.1 Grouping and Methods

110 SPF level SD rats, male, weight 160-180 g, were fed for one week adaptively. 10 rats were selected as normal control group and fed with regular diet; the rest animals were fed with high fat diet. After feeding continuously for 4 weeks (blood was drawn at regular intervals to test for the four indexes of blood lipids, in order to determine whether models were successful), 100 successfully modeled animals in relatively good conditions were chosen and evenly separated into 10 groups based on blood lipid levels and weights: 10 rats per group, named as hyperlipidemia model control group (administered with distilled water), S1 group, S2 group, S3 group, S4 group, S5 group, S6 group, D1 group, D2 group, and D3 group.

After feeding high fat diet for 4 weeks, drugs were administered according to the above grouping with high fat diet continuously provided (the normal control group was fed with normal diet), drugs were administered once per day, for a period of 4 W. After the last drug administration, animals were kept overnight fasting, weighed the next day, then anaesthetized using chloral hydrate, after drawing blood through inferior vena cava, animals were executed. Supernatant was obtained by centrifuging the blood samples, then serum biochemical indexes were measured.

2.2 Measurements

1) Regular observation was performed, and weights were recorded every week.

2) Rat serum lipid indexes of each group: blood was drawn from orbital venous plexus every 2 weeks, serum was separated for the detection of: total cholesterol (TC), triglyceride (TG), high-density lipoprotein cholesterol (HDL-C), and low-density lipoprotein cholesterol (LDL-C).

2.3 Results

The effects on serum TC, TG, HDL-C, LDL-C, and TC/HDL-C are shown in Tables 6 and 7. As shown in Table 6, after feeding with high fat diet for 4 W, the model control group rats showed significantly elevated levels of TC and LDL-C ($p<0.01$), and significant increase in TG ($p<0.05$), compared to those of normal control group, indicating successful modeling of hyperlipidemia rats. Rats were evenly separated into 4 groups according to blood lipid level. As can be seen from Table 7, after 4 W drug administration, drug samples of S1-S6 groups and D1 group lowered TC, TG and LDL-C levels in serum ($p<0.05$ or $p<0.01$), compared to the model control group.

TABLE 6

Serum lipid data of successfully modeled evenly grouped rats ($\bar{x} \pm S$)

| Group | n | TC (mmol/L) | TG (mmol/L) | HDL-C (mmol/L) | LDL-C (mmol/L) |
|---|---|---|---|---|---|
| Normal control group | 10 | 1.32 ± 0.18 | 1.68 ± 0.64 | 0.58 ± 0.06 | 0.33 ± 0.04 |
| Model control group | 10 | 2.10 ± 0.36## | 2.26 ± 0.43## | 0.61 ± 0.07 | 0.45 ± 0.08## |
| S1 group | 10 | 2.08 ± 0.33 | 2.27 ± 0.36 | 0.58 ± 0.09 | 0.45 ± 0.07 |
| S2 group | 10 | 2.11 ± 0.39 | 2.28 ± 0.54 | 0.61 ± 0.11 | 0.43 ± 0.08 |
| S3 group | 10 | 1.96 ± 0.42 | 2.25 ± 0.67 | 0.59 ± 0.08 | 0.45 ± 0.09 |
| S4 group | 10 | 1.99 ± 0.38 | 2.28 ± 0.58 | 0.60 ± 0.10 | 0.46 ± 0.07 |
| S5 group | 10 | 2.10 ± 0.43 | 2.23 ± 0.61 | 0.58 ± 0.09 | 0.45 ± 0.10 |
| S6 group | 10 | 2.04 ± 0.37 | 2.26 ± 0.45 | 0.59 ± 0.07 | 0.43 ± 0.08 |
| D1 group | 10 | 2.03 ± 0.42 | 2.25 ± 0.53 | 0.61 ± 0.11 | 0.45 ± 0.07 |
| D2 group | 10 | 1.98 ± 0.37 | 2.26 ± 0.57 | 0.60 ± 0.08 | 0.45 ± 0.10 |
| D3 group | 10 | 1.99 ± 0.39 | 2.28 ± 0.53 | 0.60 ± 0.09 | 0.44 ± 0.07 |

Note:
compared to normal control group: #$p < 0.05$, ##$p < 0.01$;
compared to model control group: $p > 0.05$ for all.

TABLE 7

Rat serum lipid data of each group after 4 W of drug administration ($\bar{x} \pm S$)

| Group | n | TC (mmol/L) | TG (mmol/L) | HDL-C (mmol/L) | LDL-C (mmol/L) |
|---|---|---|---|---|---|
| Normal control group | 10 | 1.24 ± 0.25 | 1.68 ± 0.51 | 0.59 ± 0.08 | 0.31 ± 0.08 |
| Model control group | 10 | 2.62 ± 0.58## | 3.04 ± 0.49## | 0.56 ± 0.09 | 0.62 ± 0.12## |
| S1 group | 10 | 2.01 ± 0.54* | 2.35 ± 0.44* | 0.58 ± 0.07 | 0.51 ± 0.11* |
| S2 group | 10 | 2.11 ± 0.42* | 2.37 ± 0.46* | 0.56 ± 0.06 | 0.53 ± 0.09* |
| S3 group | 10 | 1.87 ± 0.56** | 2.07 ± 0.38** | 0.60 ± 0.07 | 0.49 ± 0.09** |

TABLE 7-continued

Rat serum lipid data of each group after 4 W of drug administration ($\bar{x} \pm S$)

| Group | n | TC (mmol/L) | TG (mmol/L) | HDL-C (mmol/L) | LDL-C (mmol/L) |
|---|---|---|---|---|---|
| S4 group | 10 | 2.04 ± 0.53* | 2.35 ± 0.38* | 0.59 ± 0.08 | 0.52 ± 0.10* |
| S5 group | 10 | 2.11 ± 0.48* | 2.32 ± 0.47* | 0.57 ± 0.07 | 0.53 ± 0.08* |
| S6 group | 10 | 2.05 ± 0.45* | 2.33 ± 0.48* | 0.59 ± 0.08 | 0.54 ± 0.09* |
| D1 group | 10 | 2.10 ± 0.34* | 2.36 ± 0.43* | 0.60 ± 0.08 | 0.55 ± 0.08* |
| D2 group | 10 | 2.38 ± 0.54 | 2.80 ± 0.48 | 0.58 ± 0.07 | 0.61 ± 0.11 |
| D3 group | 10 | 2.46 ± 0.49 | 2.79 ± 0.59 | 0.59 ± 0.08 | 0.60 ± 0.10 |

Note:
compared to normal control group: #p < 0.05, ##p < 0.01;
compared to model control group: *p < 0.05, **p < 0.01.

3. Conclusion

S1-S6 and D1 showed clear effects in lowering blood lipid levels in hyperlipidemia rat models, and the compositions of S1-S6 exhibited synergistic or enhanced effects in lowering blood lipids.

Example 7 Test of Lowering Blood Pressure

Materials and Methods

1) Samples and solution: samples from Test Samples 1-6 and Control Samples 1-3 were labeled as S1, S2, S3, S4, S5, S6, and D1, D2, D3, respectively; 0.9% NaCl injection (physiological saline), pack size: 250 mL/bottle, Sichuan Kelun Pharmaceutical Co. Ltd., lot#: C13102005-1; distilled water, and picric acid, etc.

2) Instruments: DKB-501A High Precision Water Bath (Shanghai Senxin Laboratory Apparatus Ltd.); electronic constant temperature drying cabinet (Changsha Medical Devices Ltd.); PowerLab/4SP ML125 non-invasive blood pressure measurement system (ML125/R NIBP, MLT1199 Disposable BP Transducer/Cable Kit; ADInstruments Ltd., Australia); MP120-1 electronic balance (Shanghai Number Two Balance Instrument Factory).

3) Experimental animals: SHR rats (SPF level), weight 190-230 g, male, provided by Beijing Vital River Laboratory Animal Technology Co. Ltd., Certificate#: SCXK (Beijing) 2012-0001. Animals were raised in SPF level barrier level animal room, animal use license#: SYXK (Guangdong) 2012-0081. WISTAR male rats (SPF level) were provided by Beijing Vital River Laboratory Animal Technology Co. Ltd., Certificate#: SCXK (Beijing) 2012-0001.

4) Dosage setting: expected dosage for human adults is 3.0 g/60 kg·BW·day. Dosage used for rats was 10 times that of human. The dosage was calculated using raw drug amount.

5) Statistic analysis: data were processed using SPSS 17.0 statistical tool, parameters were displayed as mean±standard deviation (0.0±S), ANOVA test was used for comparison among groups, p<0.05 was defined as statistically significant.

Methods and Results 9-10 week old male spontaneously hypertensive rats (SHR) were randomly separated into 10 groups, 10 rats per group, named as hypertension model control group (administered with distilled water), S1 group, S2 group, S3 group, S4 group, S5 group, S6 group, D1 group, D2 group, and D3 group. 10 normal WISTAR rats were selected as normal control group (administered with distilled water). Animals in each group were intragastrically administered with different dosages of drugs, once per day, for a period of 4 W. Rat caudal artery blood pressure (systolic arterial pressure, SAP, mmHg) was measured using non-invasive caudal artery blood pressure measurement system, before and after 4 W treatment.

Non-invasive tail cuff method (NIBP): a rat was placed into the rat fixer, allowing its tail exposed. Infrared heater was set to be 38° C. Rat tail was heated under radiation for about 10 mins until the tail becoming soft and caudal artery expanding sufficiently. Pressured tail cuff was passed through the rat tail and fixed at the tail root, so that rat caudal artery was in tight contact with the pulse sensor of the PowerLab ML125/Rnon-invasive caudal artery blood pressure measurement system. The pulse waveform was monitored, and blood pressure could be measured when stable pulse wave appeared. When the animal calmed down, pressure was increased in the tail cuff at 90-420 BPM (rat pressure increasing level), pulse wave could be seen to gradually diminish until disappear, then gas was gradually released in the tail cuff, pressure gradually decreased in the tail cuff, and pulse wave reappeared when the pressure reached SAP, the blood pressure of which was defined as the rat tail SAP. The measurement was repeated for 3 times, and average value was obtained. The pressure drop value (blood pressure drop value) was calculated as SAP after treatment minus SAP before treatment. The result is shown in Table 8.

TABLE 8

The effect of samples on blood pressure (SAP, mmHg) of SHR rats ($\bar{x} \pm S$)

| Group | n | Blood pressure before treatment (SAP, mmHg) | Blood pressure after 4 W treatment (SAP, mmHg) |
|---|---|---|---|
| Normal control group | 10 | 108.45 ± 16.27 | 114.72 ± 17.48 |
| Model control group | 10 | 175.65 ± 14.45# | 186.27 ± 13.71# |
| S1 group | 10 | 174.53 ± 15.38 | 171.24 ± 15.56* |
| S2 group | 10 | 176.12 ± 14.78 | 170.45 ± 13.88* |
| S3 group | 10 | 175.49 ± 14.18 | 166.80 ± 15.58* |
| S4 group | 10 | 174.43 ± 15.64 | 170.86 ± 16.41* |
| S5 group | 10 | 175.49 ± 14.85 | 171.34 ± 13.56* |
| S6 group | 10 | 174.76 ± 14.91 | 170.78 ± 14.98* |
| D1 group | 10 | 175.24 ± 13.37 | 174.25 ± 13.95* |
| D2 group | 10 | 176.45 ± 15.79 | 180.90 ± 17.84 |
| D3 group | 10 | 174.85 ± 15.92 | 179.78 ± 15.60 |

Note:
compared to normal control group: #p < 0.01;
compared to model control group: *p < 0.05.

The result showed that, rats in the model control group had significantly elevated blood pressure compared to that of rats in the normal control group, indicating spontaneously hypertensive rats as successful models. SHR rats in S1-S6 groups and D1 group showed significantly lowered blood pressure after 4 W drug treatment (p<0.05), compared to that of model control group.

3. Conclusion

S1-S6 and D1 samples showed significant effects in lowering blood pressure, and the compositions of S1-S6 exhibited synergistic or enhanced effects in lowering blood pressure.

Example 8 In Vivo Efficacy Determination

Animal subjects or human subjects are assigned randomly into a control group and a treatment group. The treatment group is provided a therapeutically effective amount of the herbal extract composition, the granule, the nutritional composition, or the pharmaceutical composition comprising (including consisting essentially of or consisting of) an extract of *Cyclocarya paliurus* leaves, Puerariae lobatae Radix and Polygonati odorati Rhizoma, with a predetermined dosage regimen over a predetermined period of time. The control group is provided with a placebo with the same dosage regimen and treatment duration. Blood glucose levels in all subjects of both experimental groups are monitored prior to the experiment, during the course of the experiment, and at the end of the experiment. Standard blood glucose kits, such as those relying on the nonspecific reducing property of glucose, and those using glucose specific enzymes, are used to monitor the blood glucose levels of the subjects. Statistical analysis is performed to compare the blood glucose levels at various time points in the course of the experiment between the control group and the treatment group, which is used along with other relevant data to determine the efficacy of the methods of treatment disclosed in the present invention.

What is claimed is:

1. A method for preparing an herbal extract composition comprising an extract of *Cyclocarya paliurus*, Puerariae lobatae Radix and Polygonati odorati Rhizoma, wherein the method comprises:
   i) providing a mixture of *Cyclocarya paliurus* leaves, Puerariae lobatae Radix and Polygonati odorati Rhizoma, wherein said mixture comprises about 30-40% (w) *Cyclocarya paliurus* leaves, about 30-40% (w) Puerariae Radix and about 20-30% (w) Polygonati odorati Rhizoma;
   ii) extracting said mixture with water to obtain an aqueous extract;
   iii) concentrating the aqueous extract to obtain a concentrated mixture;
   iv) obtaining a liquid portion of said concentrated mixture; and
   v) drying said liquid portion to produce an herbal extract composition.

2. A method for preparing a granule comprising an herbal extract composition comprising an extract of *Cyclocarya paliurus*, Puerariae lobatae Radix and Polygonati odorati Rhizoma and an excipient, wherein said method comprises:
   i) providing the herbal extract composition, wherein the herbal extract composition comprises about 30-40% (w) *Cyclocarya paliurus* leaves, about 30-40% (w) Puerariae Radix and about 20-30% (w) Polygonati odorati Rhizoma;
   ii) mixing said herbal extract composition with an excipient to obtain a mixture;
   iii) treating a portion of said mixture with an alcoholic solvent to obtain a wet granule; and
   iv) drying the wet granule to obtain a dry granule.

3. The method according to claim 2, wherein the excipient is mannitol.

4. The method according to claim 2, wherein the alcoholic solvent is 95% ethanol.

5. The method of claim 2, wherein the herbal extract composition comprises about 35% (w) *Cyclocarya paliurus* leaves, about 35% (w) Puerariae lobatae Radix and about 30% (w) Polygonati odorati Rhizoma.

6. The method of claim 2, further comprising filtering the herbal extract through a filter.

7. The method of claim 2, further comprising removing heavy metal from the herbal mixture.

* * * * *